(12) United States Patent
Muellinger et al.

(10) Patent No.: US 8,834,848 B2
(45) Date of Patent: Sep. 16, 2014

(54) FLOW AND VOLUME REGULATED INHALATION FOR TREATMENT OF SEVERE ORAL CORTICOSTEROID-DEPENDENT ASTHMA

(75) Inventors: Bernard Muellinger, Munich (DE); Gerhard Scheuch, Wohrathal (DE); Thomas Hofmann, Doylestown, PA (US); Philipp Kroneberg, Olching (DE)

(73) Assignee: Activaero GmbH Research & Development, Gauting (DE)

( * ) Notice: Subject to any disclaimer, the term of this patent is extended or adjusted under 35 U.S.C. 154(b) by 0 days.

(21) Appl. No.: 13/605,451

(22) Filed: Sep. 6, 2012

(65) Prior Publication Data

US 2013/0037024 A1 Feb. 14, 2013

Related U.S. Application Data

(63) Continuation-in-part of application No. 13/147,761, filed as application No. PCT/EP2010/051321 on Feb. 3, 2010, now Pat. No. 8,668,901, which is a continuation-in-part of application No. 12/365,754, filed on Feb. 4, 2009, now abandoned.

(51) Int. Cl.
*A61K 9/00* (2006.01)
*A61M 11/06* (2006.01)
*A61M 16/00* (2006.01)

(52) U.S. Cl.
CPC ...... *A61K 9/0078* (2013.01); *A61M 2016/0027* (2013.01); *A61M 2205/502* (2013.01); *A61M 11/06* (2013.01); *A61M 2016/0024* (2013.01); *Y10S 514/862* (2013.01); *Y10S 514/958* (2013.01)
USPC ............... 424/43; 424/45; 424/400; 424/489; 128/200.16; 128/200.2; 128/203.13; 128/203.15; 514/127; 514/169; 514/170; 514/862; 514/958; 600/538

(58) Field of Classification Search
USPC ................. 424/43, 45, 400, 489; 128/200.16, 128/200.2, 203.13, 203.15; 514/127, 169, 514/170, 862, 958; 600/538
See application file for complete search history.

(56) References Cited

U.S. PATENT DOCUMENTS 6,187,765 B1 2/2001 Harris et al.
6,401,710 B1 6/2002 Scheuch et al.
(Continued)

FOREIGN PATENT DOCUMENTS

WO 2010043981 A1 4/2010

OTHER PUBLICATIONS

Kohler et al., "Lung Deposition after electronically Breath-Controlled Inhalation and Manually Triggered Conventional Inhalation in Cystic Fibrosis Patients," 2005, Journal of Aerosol Medicine, 18(4):386-395.*

(Continued)

*Primary Examiner* — Jane C Oswecki
(74) *Attorney, Agent, or Firm* — Peters Verny, LLP

(57) ABSTRACT

A drug and device combination system used in a method for treatment of patients suffering from severe and oral corticosteroid-dependent asthma and other respiratory diseases requiring a treatment with orally administered steroids. The method for administration of the inhalable corticosteroid by a flow rate and volume regulated inhalation. The combination system of the inhalable corticosteroid and the device for regulating flow rate and volume of the inhalable corticosteroid and thus achieving delivery of said inhalable corticosteroid into the small airways of the lungs. The individually programmable device that assures safe and reproducible corticosteroid delivery compliant with treatment protocol.

21 Claims, 13 Drawing Sheets

Complete Oral Corticosteroids Weaning

(56) References Cited

U.S. PATENT DOCUMENTS

| | | | |
|---|---|---|---|
| 6,463,929 | B1 | 10/2002 | Scheuch et al. |
| 6,571,791 | B2 | 6/2003 | Scheuch et al. |
| 6,606,989 | B1 | 8/2003 | Brand et al. |
| 6,681,762 | B1 | 1/2004 | Scheuch et al. |
| 7,077,125 | B2 | 7/2006 | Scheuch |
| 2001/0037806 | A1 | 11/2001 | Scheuch et al. |
| 2005/0087189 | A1* | 4/2005 | Crockford et al. ....... 128/203.15 |
| 2006/0201499 | A1 | 9/2006 | Muellinger et al. |
| 2007/0006883 | A1 | 1/2007 | Kolb et al. |
| 2007/0020299 | A1* | 1/2007 | Pipkin et al. .................. 424/400 |
| 2008/0020299 | A1 | 1/2008 | Lee |

OTHER PUBLICATIONS

Griese et al., "Improvement of Alveolar Glutathione and Lung Function But Not Oxidative Stress in Cystic Fibrosis," Jan. 15, 2004, Am. J. of Respiratory Critical Care Medicine, 169(15): 822-828.*

Nelson et al "Fluticasone Propionate Powder: Oral Corticosteroid-Sparing Effect and Improved Lung Function and Quality of Life in Patients with Severe Chronic Asthma," Feb. 1999, J. Allergy Clin. Immunol., 103:2Pt 1:267-275.*

Scheuch et al., "Novel Approaches to Enhance Pulmonary Delivery of Proteins and Peptides," Nov. 1, 2007; J. Physiology and Pharmacology; Polish Physiological Society, Krakow, PL; V58/suppl. 5(2):615-625.*

Adams, N., et al., "Inhaled Fluticasone Versus Inhaled Beclomethasone or Inhaled Budesonide for Chronic Asthma", Cochrane Database of Systematic Reviews, (2):CD002310 (2004) Update in Cochrane Database of Systematic Reviews, (1):CD002310 (2002).

Adams, N., et al., "The Dose-Response Characteristics of Inhaled Corticosteroids When Used to Treat Asthma: An Overview of Cochrane Systematic Reviews", Respiratory Medicine, 100/8:1297-1306, (2006).

Adams, N.P., et al., "Inhaled Fluticasone at Different Doses for Chronic Asthma in Adults and Children", Cochrane Database of Systematic Reviews, (3):CD003534 (Jul 20, 2005): Update of Cochrane Database of Systematic Reviews, (1):CD003534 (2002).

Briese, M., et al., "Improvement of Alveolar Glutathione and Lung Function But Not Oxidative State in Cystic Fibrosis", Am. J. of Respiratory Critical Care Medicine, Jan. 15, 2004, 169/15:822-828, XP009133675, Abst., p. 822, col. 2, Para. 5, p. 826, col. 1, Para. 4, p. 827, col. 2, Para. 2.

Dempsey, O. J., et al., "Relative Lung Delivery of Fluticasone Propionate via Large Volume Spacer of Nebuliser in Healthy Volunteers", Eur. J. Clin. Pharmacol., 57/9:637-41 (2001).

Global Initiative for Asthma, Global Strategy for Asthma Management and Prevention, pp. 59-61 (2008).

Hansel, T. T., et al., A Multinational, 12 week, "Randomized Study Comparing the Efficacy and Tolerability of Ciclesonide and Budesonide in Patients with Asthma", Clinical Therapeutics, Excerpta Medica, Princeton, NJ, Jun. 1, 2006, 28/6:906-920, XP025059785ISSN: 0149, retrieved on Jun. 1, 2006, p. 917, col. 2, Para. 1.

Hayasaka, Naomi, et al., "Optimization of Dosing Schedule of Daily Inhalant Dexamethasone to Minimize Phase Shifting of Clock Gene Expression Rhythm in the Lungs of the Asthma Mouse Model", Endocrinology, Jul. 2007, 148/7:3316-3326, XP002582647.

Karagiannidis, C, et al., "High-Altitude Climate Therapy Reduces Local Airway Inflammation and Modulates Lymphocyte Activation", Scand. J. Immunol., p. 304 (2006).

Nelson, H. S., et al., "Fluticasone Propionate Powder: Oral Corticosteroid-Sparing Effect and Improved Lung Function and Quality of Life in Patients with Severe Chronic Asthma", J. Allergy Clin. Immunol., 103:2Pt 1:267-75 (Feb. 1999).

PCT/EP2010/051321, International Search Report and Written Opinion, Jun. 8, 2010.

Pocket Guide for Asthma Management and Prevention, Global Initiative for Asthma, A Pocket guide for Physicians and Nurses, pp. 1-28 (2008).

Powell, H., et al., "High Dose Versus Low Dose Inhaled Corticosteroid as Initial Starting Dose for Asthma in Adults and Children", Cochrane Database of Systematic Reviews, (2003), Issue 4, Art. No. CD004109. DOI: 10/10002/14651858. CD004109, pub. 2.

Scheuch, G., et al., "Novel Approaches to Enhance Pulmonary Delivery of Proteins and Peptides", Journal of Physiology and Pharmacology, Polish Physiological Society, Krakaw, PL., Feb. 2010, V58/supple. 5, No. 2., pp. 615-625, XP009128918, ISSN: 0867-5910, Abstract, p. 621, last paragraph.

Ververeli, K., et al., "Oral Corticosteroid-Sparing Effects of Inhaled Corticosteroids in the Treatment of Persistent and Acute Asthma", Annals of Allergy, Asthma and Immunology, 92/5:512-522(11), (May 2004).

Westbroek, J., et al., "Oral Steroid-sparing Effect of Two Doses of Nebulized Fluticasone Propionate and Placebo in Patients with Severe Chronic Asthma", Resp. Med., 93/10:689-99, (Oct. 1999).

JP 2011-548677 Applicant's response to Final Rejection, Jun. 16, 2014.

CN 201080006616.X Final Rejection, Apr. 16, 2014.

Kohler, Elke, Ph.D., et al., "Lung Deposition after electronically Breath-Controlled Inhalation and Manually Triggered Conventional Inhalation in Cystic Fibrosis Patients", Journal of Aerosol Medicine, 18/4:386-395, (2005).

Muellinger, B., et al. "Drug Output Of Inhalers Is Not A Predictor Of Lung Dose," Nov. 5, 2008, Activaero GmbH, http://www.akita-jet.de/fileadmin/user_upload/AKITA_JET/Publikationen/ IDD_2008_AKITA_JET_Poster_2008-11-05_V0_0_1.pdf.

JP 2011-548677 Final Rejection, Dec. 6, 2013.

* cited by examiner

Flow and Volume Controlled Drug Deposition

Figure 12

Oropharyngeal Drug Deposition

Flow rate and Volume Regulated Inhalation

Unregulated Inhalation

Figure 13A-B

FLOW AND VOLUME REGULATED INHALATION FOR TREATMENT OF SEVERE ORAL CORTICOSTEROID-DEPENDENT ASTHMA

CROSS-REFERENCE TO RELATED APPLICATION

This application is a Continuation-in-Part of the U.S. patent application Ser. No. 13/147,761 filed on Oct. 19, 2011, now U.S. Pat. No. 8,668,901 based on the PCT application PCT/EP2010/051321 having the International Filing Date Feb. 3, 2010, and is Continuation-in-Part of the U.S. patent application Ser. No. 12/365,754 filed on Feb. 4, 2009 (ABN). The above patent applications are hereby incorporated herein by reference.

BACKGROUND OF THE INVENTION

1. Field of the Invention

This invention concerns generally a drug and device combination system used in a method for treatment of severe and oral corticosteroid-dependent asthma and other respiratory diseases requiring a treatment with orally administered steroids. The method comprises administration of an inhalable corticosteroid drug by a flow rate and volume regulated inhalation wherein the inhalable corticosteroid is administered predominantly into a target area of the lungs, in particular the small airways of the lungs, using a system comprising an inhalable drug and device combination. The system permits fine tuning of the flow of the inhalable corticosteroid drug into the lungs in an optimized volume to secure a maximal and reproducible corticosteroid dose deposition into the lung target area. Both the method and the system are safe, efficacious, reproducible, controllable and individually programmable to assure treatment safety and compliance. The device's capability to control flow rate and inhalation volume assures delivery of the inhalable drug directly to the target area of the lungs and thereby minimizes the drug dose requirement of oral steroids while at the same time it maximizes the drug dose deposition in said target areas, assures the dose reproducibility, decreases drug waste and eliminates or greatly reduces side effects.

The drug and device combination system has unexpectedly large clinical benefits. When the patients are treated with this system according to the method of the invention and when the protocol of the invention for inhalable corticosteroids delivery is followed, the use of the drug and device combination system results in a complete weaning of the patients from oral corticosteroids in at least 50% of all treated patients, or in a partial weaning to ≤50% of the initial oral corticosteroid dose in about 80% of all treated patients. Concurrently, it results in a substantial improvement of FEV1—as well as in a clinically meaningful improvement of Quality of Life of these patients. There is a decreased degree of symptoms exacerbation and a decreased need for hospitalization. The device that provides a controlled and regulated flow rate and volume during inhalation assures a more homogeneous peripheral deposition of the drug, and its individually tailored programming based on the patient's health conditions provides a feedback regarding the adherence to the treatment protocol.

The method and system of the invention are particularly suitable for delivery of inhalable corticosteroids into the peripheral small airways of the lungs for treatment of severe and oral corticosteroid-dependent asthma and other respiratory diseases requiring treatment with oral corticosteroids, without the need for simultaneous administration of oral corticosteroids or with a significantly decreased need for such simultaneous administration of oral corticosteroids. The controlled flow rate and volume system significantly increases delivery of the drug and selectively delivers the aerosolized inhalable corticosteroid into the small airways, particularly to terminal and respiratory bronchioles and alveolar ducts and sacks of the peripheral lungs. It further eliminates or significantly decreases deposition of the corticosteroid into the larger bronchioles, bronchi and trachea of the upper lungs as well as into the oropharyngeal area and thereby substantially decreases or completely eliminates undesirable secondary symptoms, such as mouth irritation, thrush, oral candidiasis, hoarseness, soreness, upper respiratory tract infection, laryngitis, voice alterations or other oropharyngeal problems typically associated with delivery of inhalable corticosteroids. The method utilizes inhalation devices comprising components for individualization of treatment parameters in patients having compromised breathing pattern due to severe and oral corticosteroid-dependent asthma or another severe respiratory disease, and for assurance of compliance and safety.

The method of the invention includes a step of complete or at least partial weaning of a patient from orally administered steroids and replacing them with much lower doses of inhalable corticosteroids, wherein the unique drug and device combination results in an unexpectedly large improvement of pulmonary function, improvement in Quality of Life, particularly in asthmatic patients, unexpected and substantial reduction of symptom exacerbations, reduction in occurrence and length of hospitalizations and in recovery of endogenous hydrocortisone (cortisol) production.

2. Background and Related Disclosures

Asthma and particularly severe oral corticosteroid-dependent asthma is a chronic inflammation of the bronchial tubes of airways that causes swelling, bronchial narrowing and constriction resulting in severe breathing obstructions in asthmatic patients. The severe form of asthma is connected with bronchial hyper-reactivity and with chronic severe and oral corticosteroid-dependent asthmatic symptoms. Other respiratory diseases that require treatment with orally administered corticosteroids experience similar symptoms. Such symptoms are generally treated with orally administered or inhalable drugs, preferably with oral or inhalable steroids and corticosteroids suitable for inhalation therapy.

Global Initiative for Asthma (GINA) asthma guidelines has been established to determine severity of the asthma. Severe and oral corticosteroid-dependent asthma is classified by GINA guidelines as steps IV and V. For step IV, the preferred treatment is to combine medium to high doses of inhaled corticosteroid with a long-acting inhaled β-agonists. For step V, the above medication is further supplemented with orally administered corticosteroids. Both treatments are known to cause or to be associated with severe side effects, which exacerbate with a continuous and extended use of high doses of inhaled corticosteroids.

Successful treatment and management of severe asthma and other respiratory diseases is often dependent on orally administered corticosteroids. Severe oral corticosteroid-dependent asthma and other respiratory diseases require treatments with high doses of orally or intravenously administered steroids that are chemically and functionally similar to hydrocortisone hormones produced by the adrenal glands. However, the long-term use of these corticosteroids leads to serious undesirable side effects, such as truncal obesity, glaucoma, acceleration of cataract formation, high blood pressure, an increased risk of diabetes due to glucose intolerance and of osteoporosis due to bone mineral loss, psychological effects, growth suppression in children and adrenal suppression. These side effects have been linked with cortisol suppression, especially when dose levels of systemically administered corticosteroids are high.

Many attempts have been made to control asthma with a particular emphasis on the control and treatment of patients suffering from the severe and oral corticosteroid-dependent asthmatic attacks. However, since each individual is unique in his/her degree of reactivity to environmental triggers, asthma affects each patient differently. This naturally influences the type, dose and route of administration of various medications and treatments.

The currently available treatments for asthma are largely dependent on the severity of the disease. In most cases (GINA step II-V), these treatments involve administration of steroids, such as orally administered corticosteroids (OCS), such as prednisone or prednisolone, or inhalable corticosteroids (ICS), such as fluticasone, beclomethasone, budenoside, mometasone, ciclesonide, flunisolide or triamcinolone acetonide, in a therapeutic dose. These treatments may be supplemented with other drugs, such as, for example, bronchodilators such as β-agonists. Since orally or otherwise systemically delivered corticosteroids affect the whole body and cause rather severe adversary side effects and secondary symptoms, locally administered corticosteroids by inhalation are highly preferred as a current treatment for asthma.

Corticosteroids, also called glucocorticoids, are powerful drugs that quickly reduce inflammation and pain. However, the corticosteroids benefit is often negated by severe side effects observed during extended administrations of corticosteroids needed for treatment of recurring respiratory diseases such as, for example, severe and oral corticosteroid-dependent asthma. To maximize benefits of corticosteroids, but minimize their potential side effects, these drugs are usually prescribed in doses as low as possible and/or only for a short duration of time. Since the severe and oral corticosteroid-dependent asthma requires repeated administration of inhalable corticosteroids, there is a real danger of developing side effects such as mouth irritation, thrush, oral candidiasis, hoarseness, sore throat, coughing, upper respiratory tract infections, laryngitis or other oropharyngeal problems as well as other serious adverse reactions tiding osteoporosis, increased mortality, poisoning from the overdose of corticosteroids or exogenous Cushing's syndrome.

Moreover, when the administration of corticosteroids is stopped or decreased too rapidly, a life-threatening acute adrenal crisis may develop because the adrenal glands of the patient are unable to produce their own hormones fast enough. Acute adrenal crisis is a state caused by insufficient levels of the steroid hormone hydrocortisone (cortisol) also called stress hormone, produced by the zona fasciculata of the adrenal gland that is released in response to any stress situation. Risk factors for acute adrenal crisis include physical stress such as infection, trauma or surgery, adrenal gland or pituitary gland injury, and premature termination of treatment with steroids.

It would therefore be advantageous to have available a method and means for replacement, or at least reduction, of orally administered corticosteroids, including weaning of the patients of corticosteroids. Such method would be particularly useful for treatment of those patients suffering from severe and oral corticosteroid-dependent asthma and who are in need of a continuous corticosteroid treatment. It would further be advantageous for reduction of side effects associated with administration of large dosages of corticosteroids, if the dose of corticosteroids administered via inhalation could further be reduced by improved targeting of aerosolized drug particles to the small airways of the deep, peripheral lung.

As indicated already above, many attempts to successfully treat severe and oral corticosteroid-dependent asthma have been made. These attempts include development of new and more potent drugs, such as for example more potent corticosteroid fluticasone as well as new nebulizing technologies that affect pulmonary drug delivery.

*Eur. J. Clin. Pharmacol.*, 57:637-41 (2001) describes a study comparing a large volume spacer and fluticasone nebulizer (FP-neb) in delivery of fluticasone propionate by inhalation in healthy volunteers. The large volume (750 ml) spacer was shown to produce about a sevenfold higher relative lung dose than nebulizer. This reference shows that the efficacy of the aerosol delivery depends on the device used for such delivery.

*Respir. Med.*, 93(10):689-99 (1999) describes the oral steroid-sparing effect of a high dose (4000 μg/day/bid) and a lower dose (1000 μg/day/bid) of inhaled fluticasone propionate. The nebulized fluticasone at a daily dose between 1 mg (1000 μg) and 4 mg (4000 μg) was a safe and effective means for reducing the oral steroids requirement of patients with chronic oral dependent asthma. The reduction in the need for orally administered prednisone was significantly greater in the group receiving 4000 μg of fluticasone propionate per day than 1000 μg per day. However, a high percentage (37%) of all patients discontinued the 4000 μg treatment, presumably for high occurrence of severe side effects.

*J. Allergy Clin. Immunol.*, 103:267-75 (1999) describes an oral corticosteroids-sparing effect and improved lung function in patients with severe chronic asthma who received 500 or 1000 μg of fluticasone propionate administered twice daily. While this treatment eliminated a need for oral prednisone, topical adverse effects associated with inhaled corticosteroids were observed during this treatment.

*Br. J. Clin. Pract.*, 48:15-8 (1994) assessed a long-term safety of fluticasone propionate in asthmatic children. Adverse effects were reported by 51% of patients even with such low doses as 50 or 100 μg administered twice a day via a dry powder inhaler.

*Cochrane Database Syst. Rev.*, (2004), Issue 3, Art. No.: CD002310 reviewed a potency of fluticasone propionate for treatment of chronic asthma and compared its effect to that of beclomethasone and budenoside. The study showed that fluticasone propionate, given at half the daily dose of beclomethasone or budenoside, resulted in improvement of forced expiratory volume in the first second (FEV1). Unfortunately, due to a larger deposition of the fluticasone in the upper lungs, it also had a higher risk of pharyngitis and other adverse side effects.

*Cochrane Database Syst. Rev.*, (2005), Issue 3, Art. No.: CD003534 describes use of inhaled fluticasone at different doses. While patients receiving 2000 μg per day of fluticasone propionate were more likely to reduce a need for oral prednisolone then those on 1500 or 1000 μg/day, hoarseness and oral candidiasis were significantly greater for these higher doses.

*Cochrane Database Syst. Rev.*, (2003), Issue 4, Art. No.: CD004109 investigated high dose versus low dose inhaled corticosteroid as initial starting dose for asthma in adults and children. 2000 μg fluticasone was administered once a day using AKITA protocol. This dose resulted in FEV1 improvement of 17.1% and reduction in oral steroid use of 33.2%. It was estimated that of the administered dose only 500-700 μg reached the central portion of the lungs, the same amount remained in the nebulizer and the remaining corticosteroid was deposited in oropharynx or exhaled. Although the FEV1 was improved with this high dose of fluticasone, the loss of the drug was approximately two-thirds of the total dose, with one third remaining in the nebulizer and one-third deposited in oropharynx thereby resulting in undesirable side effects.

*Respiratory Medicine*, 94: 1206-1214 (2000) investigated the efficacy and safety of nebulized fluticasone propionate compared to orally administered prednisolone. The nebulized fluticasone was at least as effective as oral prednisolone in the treatment of children with acute exacerbated asthma.

*Annals Allergy, Asthma and Immunology*, 92:512-522 (2004) reviewed the efficacy and safety of inhaled corticosteroids when used to reduce daily oral corticosteroid requirement in patients with severe asthma. Authors concluded that inhalable corticosteroid can reduce orally administered corticosteroids requirements in patients with persistent and exacerbated asthma. However, the question of increased adverse side effects still remains.

The US patent application publication No.: 20050087189 A1 describes an inhalation device which emits aerosol only during the first half of the patient's inspiration time which is used to administer budesonide to asthmatic children. The results suggested that lower daily doses could be used and that the compliance was better than in case of nebulizers which emit aerosol continuously. However, US 20050087189 A1 does not disclose any flow rate and/or volume control of the device. It is further not disclosed that any of the children could be weaned from any orally administered corticosteroids partially or completely, using the device and method described in US 20050087189 A1.

*Respir. Med.,* 86(2):105-8 (1999) demonstrated, in an open label-study, that a nominal dose of 4-8 mg budesonide daily, given via conventional nebulizer (which was not specified in the publication) will, over a period of 12-18 months, lead to steroid weaning in 14 of the 18 subjects studied. There were also only moderate improvements in pulmonary function, along with a reduction of the mean annual number of asthma exacerbations requiring hospitalization, from 1.5 to 0.9 per year. The relatively high dose (up to 8 mg) and volume in the nebulizer (16 mL) will demand very long inhalation times of more than 30-35 min per treatment. In addition, side effects like oral thrush or disturbing sore throat occurred in 11% of the subjects treated. Milder side effects such as hoarseness and mild thrush were also reported, but not quantified.

The above discussed disclosures concern administrations of steroids to asthmatic patients and efficacies thereof in reducing the concurrent use of orally administered steroids. These disclosures indicate that the need for orally administered steroids in patients suffering from severe and oral corticosteroid-dependent asthma may be decreased by administration of appropriately high doses of inhalable corticosteroids. However, when such high doses of inhalable corticosteroids are administered, severe adverse side reactions still occur, preventing a truly efficacious treatment of these patients.

It would be therefore advantageous to have available a controlled system comprising a drug and device combination and a method including a treatment protocol that would assure compliance with preset treatment conditions. Such system would provide and assure delivery of an efficacious dosage of the inhalable corticosteroid to small airways of the deep peripheral lung predetermined target area, without at the same time depositing the drug in oropharyngeal area in order to reduce or eliminate undesirable adverse side reactions and secondary symptoms. Clearly, such system would depend on the exclusive and precise delivery of these drugs to said target area of the lungs and also on inhalation devices and apparatuses used for such delivery. Numerous attempts were made to provide devices for precise administration of drugs to the lungs; however, these attempts lack efficacy, targeted delivery to deeper lung areas, elimination of adverse reactions and individualization of such treatment.

In this regard, U.S. Pat. No. 6,606,989 discloses a device for precise administration of medicated aerosol to the lungs. The device comprises of an inhalation mouthpiece; a pressure sensor responsive to a suction pressure to produce a triggering signal; an adjustable vaporizer coupled to the inhalation mouthpiece containing the inhalable fluid that issues frequencies to deliver the vaporized fluid to the mouthpiece; a compressed-air control valve responsive to a valve signal to provide a predetermined inhaled volume; a volumetric flow controller coupled to the compressed-air control valve to preset a determined quantity of a volumetric flow of the nozzle flow; a flow meter for control of a predetermined volumetric flow; and an electronic controller that receives the triggering signal from the pressure sensor to produce the valve signal and the vaporizing signal. The electronic controller is configured with a pre-settable vaporizing period and a pre-settable pause interval. It further controls the high frequencies issued by the vaporizer and is operable to set the vaporizing period of the adjustable vaporizer to an invariable value from opening of the compressed-air control valve and causes a predetermined volume to be emitted at the device's mouthpiece for each respiratory maneuver. While this disclosure certainly provides a useful device for inhalation, it lacks the aerosol having a limited particle size range permitting targeted delivery of the drug into the peripheral lungs and does not provide an individual control for compliance with the drug delivery protocol. Moreover, U.S. Pat. No. 6,606,989 does not disclose any specific values for flow rate and/or volume which would improve the deposition of aerosolized particles in the target area of the lower lungs, in particular the small airways.

*J. Physiol. Pharmacol.,* 58 (Supp1.5): 615-625 (2007) describes novel approaches to enhance pulmonary delivery of proteins and peptides. This article describes importance of a number of biophysical and physiological parameters that have to be considered when the delivery of proteins and peptides into systemic circulation is contemplated. Among these parameters are particle diameter, particle density, hygroscopicity, electrical charge, chemical properties of the drug, age of the patient, pulmonary disease, breathing pattern, all of which affect the mechanism of pulmonary drug deposition. The article discloses one type of the AKITA® inhalation systems that guides the patient through the inhalation maneuver and ensures an optimized particle deposition.

For treatment of severe and oral corticosteroid-dependent asthma, the above devices might be somehow useful; however, to achieve the reduction or elimination and weaning of the patient from the orally administered corticosteroids, these devices are not efficacious enough without further modifications, adjustments, additional components and without a precise protocol for inhalable corticosteroids delivery.

It would, therefore, be advantageous to have available a combination system including an inhalation device, an inhalable corticosteroid and a method that would provide efficacious treatment for severe and oral corticosteroid-dependent forms of asthma with an efficacious dose of said inhalable corticosteroid selectively deposited at a site of asthmatic inflammation, namely in alveoli and bronchioles of the small airways of the lower, peripheral lungs, combined with no or low deposition of the corticosteroid in the nose, mouth, throat, oropharyngeal area, larger bronchioles, bronchi, and trachea, wherein the need for concurrent orally administered steroids could be eliminated or the need for the oral dose of these drugs could be at least significantly reduced in the oral corticosteroid-dependent asthma patient population. As a consequence, the oropharyngeal side effects enumerated above will be reduced.

It is, therefore, a primary object of this invention to provide a combination system including an inhalation device, an inhalable corticosteroid, a method for treatment and a protocol for precise and efficacious delivery of said inhalable corticosteroid into the small airways of the lungs for the treatment of severe and oral corticosteroid-dependent forms of asthma and other respiratory diseases. The system delivers a sufficiently high dosage of the inhalable corticosteroid to treat these conditions, including severe and corticosteroid-dependent asthma, to permit either a complete elimination and weaning of the patients from oral corticosteroids in at least 50% of all treated patients or reduction of the oral corticosteroid dose in about 80% of all patients, with a mean reduction of the initial dose of about 75%. Additionally, said system achieves a maximal deposition of the inhalable corticosteroid in the lower, peripheral lung, controlled dose reproducibility, reduced variability of lung dose deposition and minimization of side effects. The system delivers the corticosteroids selectively into the small airways of the peripheral lungs (also called lower lungs) of an asthmatic patient without depositing said inhalable corticosteroid into the upper lungs, trachea, mouth, nose or oropharyngeal cavity, and thus without causing undesirable side effects, and it greatly improves the physiological parameters of treated patients.

SUMMARY

One aspect of the current invention is a drug and device combination system used in a method for treatment of severe and oral corticosteroid-dependent asthma and other respiratory diseases that require a concurrent treatment with orally or otherwise systemically administered corticosteroids wherein said treatment with said system results in either complete weaning from or substantially decreased use of said orally administered corticosteroids in a patient suffering from severe and oral corticosteroid-dependent asthma or another respiratory disease.

Another aspect of the current invention is a drug and device combination system providing means for increased efficacy of an inhalable corticosteroid treatment by delivering therapeutically effective dosages of inhalable corticosteroid selectively to small airways, including terminal bronchioles, respiratory bronchioles, alveolar ducts and alveolar sacs of the lower lungs of a patient suffering from severe and oral corticosteroid-dependent asthma, without causing adverse side effects and secondary symptoms by incidental delivery of these corticosteroid to a mouth or nose cavity, throat and upper lungs.

Another aspect of the current invention is a drug and device combination system having unexpectedly large clinical benefits in treatment of patients suffering from severe asthma or another respiratory disease that requires concomitant oral corticosteroid treatment in that that when these patients are treated with the system according to the method of the invention and following the protocol of the invention for inhalable corticosteroid delivery, such treatment results in a complete weaning of the patients from oral corticosteroids in at least 50% of all treated patients, or in a partial weaning to ≤50% of the initial oral corticosteroid dose in about 80% of all treated patients, said treatment additionally resulting in a substantial improvement of FEV1 after 18 weeks of treatment, such as by more than 16% in the group treated with the full dose of budesonide (1 mg), in improvement of Quality of Life of these patients, in a decreased degree of symptoms exacerbation and a decreased need for hospitalization, and wherein the system's device provides a controlled and regulated flow rate and volume during inhalation that assures more homogeneous peripheral deposition of the drug in the small airways of the lungs and wherein said device also provides individually tailored programming to the patient's health conditions and at the same time provides a feedback for and assures the adherence of the patient to the treatment protocol.

Still another aspect of the current invention is a drug and device combination system used in a method for treatment of severe and oral corticosteroid-dependent asthma wherein said device of the system regulates the flow rate and volume of the aerosol containing the inhalable corticosteroid, thereby resulting in the delivery of said inhalable corticosteroid predominantly into a target area of the lower lungs, in particular the small airways, thereby resulting in delivery of said inhalable corticosteroid in efficacious quantity sufficient for a complete weaning of the patient from the orally administered corticosteroid drugs and hence elimination of the need for use of such orally administered drugs in at least 50% of all treated patients.

Still yet another aspect of the current invention is a drug and device combination system used in a method for treatment of severe and oral corticosteroid-dependent asthma wherein said device of the system regulates the flow rate and volume of the aerosol containing the inhalable corticosteroid, thereby resulting in the delivery of said inhalable corticosteroid predominantly into the target area of the lower lungs, in particular the small airways, and thereby resulting in delivery of said inhalable corticosteroid in efficacious quantity that is sufficient for at least 50% reduction of the initial oral corticosteroid dose in about 80% of all treated patients suffering from severe and oral corticosteroid-dependent asthma or from another corticosteroid-dependent respiratory disease.

Still yet another aspect of the current invention is a drug and device combination system used in a method for treatment of severe oral corticosteroid-dependent asthma wherein said device of the system regulates the flow rate of the aerosol to about 100-400 ml per second, preferably 200 ml per second, and wherein said device of the system regulates the inhalation volume to about 400-2000 ml, preferably between about 1000 ml and about 2000 ml, most preferred about 1400 ml, by using an electronically controlled inhalation system, optionally with overpressure from about 0.1 mbar up to 40 mbar, further providing said aerosol with mean particle sizes predominantly from about 1 to about 5 μm, and thereby resulting in the delivery of said inhalable corticosteroid predominantly into the target area of the small airways of the lower lungs, wherein said system further enables such delivery to be achieved in less than 14 minutes, preferably less than 10 minutes and most preferably in from 6 to 8 minutes, and wherein said inhalation system further comprises a pre-programmable therapeutic protocol card for patient individualization of the treatment protocol and for the assurance of compliance with such protocol.

Yet another aspect of the current invention is a method for treatment of severe, oral corticosteroid-dependent asthma and other oral corticosteroid-dependent respiratory diseases with a nebulized inhalable corticosteroid drug selected from the group consisting of budenoside, fluticasone, beclomethasone dipropionate, mometasone furoate, ciclesonide, flunisolide or triamcinolone acetonide wherein the clinical effect is reached with minimum efficacious amount of precisely targeted drug to the small airways of the lungs and with eliminated or greatly diminished systemic and local extrathoracic or oropharyngeal side effects.

Still yet another aspect of the current invention is a method for treatment of severe, oral corticosteroid-dependent asthma by using a drug and device combination system for inhalation of nebulized budenoside, delivered into the target area of the lower lungs using an electronically controlled inhalation system, optionally comprising a jet nebulizer, and optionally enabling the application of an overpressure from above zero, such as 0.1 mbar, up to 40 mbar during inhalation wherein the concentration of budesonide in the aerosolizable drug composition is from about 0.1 to 2 mg/ml, preferably from 0.25 to about 1 mg/ml, with the total dose of budesonide not exceeding about 4 mg, and with the resulting deposition of said budenoside into the target area of the lower lungs being at least 0.2 mg or more, achieved in less than 14 minutes, preferably in from 6 to 10 minutes.

Still another aspect of the current invention is a method for treatment of severe, oral corticosteroid-dependent asthma by providing an inhalation system for individualization of the treatment wherein said inhalation system comprises a pre-programmable inhalation volume, flow rate and overpressure, and a compliance monitoring system which allows the patient and the doctor to see and control the adherence of the patient to the treatment protocol including a date, onset and duration of each single inhalation treatment, timing of inhalation, such as for example, morning or evening, inhaled dose per day, chosen inhalation volume setting and changes thereof, number of breaths taken, data on whether each single inhalation treatment was finished or interrupted, missed treatments and other therapeutic parameters, wherein such means are or may be any storage media, a smart card, a chip or a wireless communication connection that permits evaluation of the treatment during and after the end of a treatment period.

Yet another aspect of the current invention is the drug and device combination system of the invention for the treatment of inflammatory lung diseases that are oral corticosteroid-dependent, namely, severe asthma, chronic obstructive pulmonary disease (COPD), cystic fibrosis (CF), sarcoidosis, chronic bronchitis, emphysema, pulmonary fibrosis, bronchiectasis, cilliary dyskinesia and other respiratory diseases.

Still yet another aspect of the current invention is a drug and device combination system for use in a method for the treatment of a patient suffering from oral corticosteroid-dependent asthma or another respiratory disease requiring a treatment with orally administered steroids, said combination comprising an inhalable corticosteroid formulation and an electronically controlled inhalation device, wherein said inhalable corticosteroid is administered to the patient as an aerosol predominantly into the small airways of the lower lungs of the patient; wherein said inhalation device is adapted to generate said aerosol to have mean particle sizes from about 1 μm to about 5 μm at a controlled flow rate preset to be from 100 ml to 400 ml/second, using a bolus technique; wherein said aerosol is administered to the small airways of the lungs in two or three phases wherein a first phase is optional and consists of administering particle-free air, wherein said first phase is followed by a second phase consisting of administration of the aerosol comprising the corticosteroid, and wherein said second phase is followed by a third phase consisting of administration of particle-free air; and wherein such administration of the inhalable corticosteroid formulation results in complete or partial weaning of the patient from the orally administered corticosteroids, and clinically meaningful increase of the FEV1-values of the patient.

Definitions

As used herein:

"Drug" means an inhalable or oral corticosteroid, glucocorticoid or steroid, as defined below.

"Corticosteroid" means an anti-inflammatory steroid hormone glucocorticoid produced endogenously in the adrenal cortex of the brain. This hormone can be reproduced synthetically.

"Glucocorticoid" means an anti-inflammatory steroid hormone that influences carbohydrate metabolisms and binds to the glucocorticoid receptor which is present in almost every vertebrate animal cell.

"Inhalable corticosteroid" means a naturally or synthetically prepared corticosteroid that is suitable for delivery by inhalation. Exemplary inhalable corticosteroids are budesonide, fluticasone, beclomethasone dipropionate, mometasone furoate, ciclesonide, flunisolide, triamcinolone acetonide and any other inhalable corticosteroid currently available or becoming available in the future.

"Oral steroid" means any steroid that is suitable for oral or systemic treatment of asthma. Representative steroids are prednisone, prednisolone, methylprednisolone, dexamethasone or hydrocortisone.

"OCS" means an oral corticosteroid.

"Small airways", "peripheral airways", "deep lungs", "lower lungs", "small lungs" or "peripheral lungs" mean an area of the lungs primarily containing terminal bronchioles, respiratory bronchioles, alveolar ducts and alveolar sacs that are a primary site of asthmatic inflammation, narrowing and constriction. This area is a "target" area for the purposes of this application. Selective and targeted deposition of an inhalable corticosteroid preferably in the target area is eminently desirable and contributes to an efficacious treatment of severe and oral corticosteroid-dependent asthma.

"Large airways", "upper lungs", "central lungs" or "large lungs" mean an upper area of lungs containing larger bronchioles, bronchi and trachea. Large depositions of an inhalable corticosteroid in this area are undesirable as they are leading to development of adverse side effects.

"Oropharyngeal area" or "extrathoracic area" means a mouth, nose, throat, pharynx and larynx. Any deposition of the inhalable corticosteroid in these areas is undesirable and leads to development of severe adverse effect such as hoarseness, loss of voice, laryngitis and candidiasis. It is preferable that there is none or only a very small residual deposition, occurring primarily during expiration of the inhaled corticosteroid, in this region.

"One breath" means a period of time when a person inhales (inspires) and exhales during a regular breathing pattern that includes inhaling and exhaling.

"Inspiration time", "inspiration period", "inspiration phase" or "inhalation time/period/phase" means a fraction of one breath when a person inhales air or, in this instance, an aerosol or aerosolized drug, such as an aerosolized corticosteroid. "Inspiration", "inspirational" or "inspiratory" and "inhalation" may be used synonymously. For purposes of this invention, the aerosolized corticosteroid is administered to an asthmatic patient during the inspiration time either without or, preferably, with an overpressure of from 0.1 to 40 mbar, to force the aerosol to the target area of the lower lungs with none or only a small amount of the drug deposition occurring in the extrathoracic area including the upper lungs and oropharyngeal area, using the protocol of the invention.

"Expiration time" means a fraction of one breath when a person exhales the air, nitric oxide or another metabolite from the lungs. For the purposes of this invention, it is preferable that the aerosolized drug is forced with a slight overpressure into the lower lungs during inspiration so that it remains in the lungs and is not exhaled during expiration time or that only a small portion of the inhaled drug is exhaled.

"Bolus technique" means transportation of the aerosol to a predefined region in the lungs by delivering an aerosol bolus during a predefined period representing a fraction of the inhalation time. The "bolus" is a large dose of the corticosteroid drug designed for rapid delivery. Thus, according to the bolus technique, drug-containing aerosol is not delivered throughout the complete inhalation time, but is emitted by the inhalation device only during a specifically selected fraction of said inhalation time. In other words, the inhalation time is divided into phases of variable duration. During a first optional phase of the inhalation time only aerosol-free air is administered. In a second phase, following the first (and sometimes referred to as the "nebulization phase" or "nebulization period"), the aerosol (i.e. the aerosolized drug) is delivered. The bout of aerosol delivered in said second phase represents the bolus. In a third phase, following the second phase, again aerosol-free air is administered to "push" the aerosol further down into the lungs and "clean" the upper lungs from aerosol, in order to reduce sedimentation of drug particles in the upper airways and decrease removal of the drug particles in the exhalation period.

"Filling dose" means the amount of a solution or suspension containing the appropriate dosage of the inhalable corticosteroid in an aqueous solvent which is filled into the nebulizer. Herein, the filling dose may contain budesonide (1 mg/2 ml or 0.5 mg/2 ml) or another inhalable corticosteroid in an appropriate dosage in, for example, about 2 ml of solvent.

"ECJN" means electronically controlled jet nebulizer.

"ECJN-Bud" means electronically controlled jet nebulizer filled with an appropriate dose of budesonide.

"CN" means a conventional jet nebulizer. Typically, a conventional nebulizer does not provide for a controlled, preset, or predefined inspiratory or inspirational flow rate or inhalation volume, and is particularly not suitable for or capable of delivering an aerosol using the bolus technique.

"CN-Bud" means a conventional jet nebulizer filled with an appropriate dose of budesonide.

"FEV1" or "$FEV_1$" means forced expiratory volume in one second either in liter or milliliter. FEV1% value is the ratio of an individual's FEV1 value to same individual's forced vital capacity value (FVC). Depending on a person's height, weight, age and sex, normal healthy FEV1 values range between about 3 and 5 liter.

"FEV1% of predicted" means FEV1 value(s) expressed as a percentage based on the predicted average FEV1 of persons having similar parameters, such as height, age, weight and sex. Such percentages are interchangeably called "FEV1% of predicted", "FEV1 (% of predicted)" or "FEV1 (% of pred.)". Healthy persons usually exhibit ~80-120% of FEV1 predicted, while patients suffering from respiratory diseases often achieve lower values. In this regard, FEV1% of predicted values are used as a means to evaluate the severity grade of a patient's lung disease, such as asthma. The FEV1% of predicted values are not to be mistaken with the "FEV1%" value which is the ratio of an individual's FEV1 value to same individual's forced vital capacity value (FVC). For the purpose of this application, the FEV1% predicted is as defined herein above, regardless whether in some other English speaking area, such definition might differ.

"VC" means vital capacity and is defined as the volume of gas that can be expelled from the lungs from a position of full inspiration, with no limit to duration of said inspiration.

"IC" means inspiratory capacity and is defined as the maximum volume of gas that can be taken into the lungs in a full inhalation after a normal, comfortable exhalation. Usually, IC-measurements are subject to larger fluctuations than FEV1 measurements, although both parameters are related lung-function parameters. Therefore, the preset inhalation volume used for the operation of the device according to this invention is chosen according to empirical data which are based on the patient's FEV1% of predicted (i.e. his/her asthma severity grade) and his/her FEV1 value, rather than being based on actual measurements of his/her IC.

"Aerosol" means a system having at least two phases, of which the continuous phase is gaseous and comprises a dispersed liquid phase in the form of small liquid droplets. Optionally, said liquid phase may itself represent a liquid solution, dispersion, suspension, or emulsion. Typically, the aerosol contains a drug that can be defined also as an active pharmaceutical ingredient, active compound or pharmaceutical and is for the purpose of this application, one of the named corticosteroids. Such aerosol is generated by, for example, a nebulizer from a liquid formulation in which the drug is dissolved, dispersed or suspended in a liquid, typically aqueous carrier. Herein, the terms "nebulized" and "aerosolized" are use synonymously.

"Particle-free air" means the air that does not contain any aerosolized drug. It is typically delivered before and/or after a bolus of the aerosolized drug when applying the bolus technique.

"Overpressure inhalation" means inhalation with actively provided air or aerosol that has a predefined flow rate and a predefined volume (ergo duration). Overpressure inhalation is typically applied during inspiration phase when the patient adjusts to the preset inspiratory flow rate as controlled by the device. If the patient's conditions, such as inflammation or constriction, result in a low inspiration volume, an overpressure of up to 40 mbar is applied during the inhalation phase to reduce the patient's inspiratory effort. Consequently, due to such overpressure, the patient is able to inspire a larger inhalation volume with a slower inspiration flow rate compared to a spontaneous inhalation. The minimum overpressure is slightly above zero, for example 0.1 mbar.

"Symptom exacerbation" means generally worsening of symptoms or conditions of a disease assessed by adverse effects.

"Asthma exacerbation" means worsening of asthma symptoms, often triggered by viral infections, and manifested through airway tightening, increased need for beta-agonists, and sometimes hospitalization. When the asthma exacerbation occurs, treatment is necessary to prevent a medical emergency, and such treatment may consist of administration of beta-agonists, steroids or antibiotics and, occasionally, also in oxygen treatment. Asthma instability due to external stimuli, allergies, smog, high altitude, etc., may be other triggers for asthma exacerbation.

"Asthma instability" means a state of the patient with asthma that is not stabilized with oral, intravenous, inhalable or otherwise administered corticosteroids or other drugs. Asthma instability can be determined and measured by asthma symptom scores, morning and evening peak expiration flow (PEF), average number of salbutamol (or another bronchodilator) puffs per day, nocturnal awakenings, Asthma Quality of Life Questionnaire (AQLQ) scores, number of days of hospitalization, and absenteeism from work or school.

"Weaning" means removing or at least reducing the need for oral corticosteroid administration and treatment. Weaning may be either instantaneous where the oral drug is removed immediately or continuous where the amount of the oral drug is slowly decreased by tapering. After weaning, the drug dose required to control a disease or a symptom is smaller than the initially required dose. Partial weaning is defined as a dose reduction to ≤50% of the initial dose (also called baseline dose). Thus, by definition, the group of partially weaned patients includes the group of completely weaned patients (also called fully weaned patients) whose dose could be reduced to zero.

"Electronically controlled jet nebulizer" means an electronically controlled jet inhalation system comprising a portable, table-top inhalation device comprising a jet nebulizer unit equipped with a mouthpiece and the container for holding the drug solution for aerosolization, said nebulizing unit further connected to a case holding the compressor, airflow pump and electronic control unit including a display, navigation and therapeutic information card for individualization of parameters for a therapeutic treatment protocol.

"Therapeutic protocol card", "therapeutic information card", or "individualized patient's treatment protocol card", means an information holding card that is a part of the device where the individualized parameters for patient's treatment are entered and logged in order to provide this information to the electronic control unit that controls the progress of each treatment. In addition, the therapeutic protocol card serves as a data storage means during the whole treatment period which allows for compliance monitoring. Therapeutic parameters stored for compliance monitoring include for example the date, onset and duration of each single inhalation treatment, timing of inhalation (morning vs. evening), inhaled dose per day, the chosen inhalation volume setting and changes thereof, the number of breaths taken, data on whether each single inhalation treatment was finished successfully or was interrupted, whether the patient inhaled too fast, whether the pressure at the mouthpiece was too high or too low, whether treatments were missed (usually hi-daily inhalation treatments), but also more technical information on the operation of the device such as error codes for certain events like "compressor damaged" or "wrong tubing attached".

"Clinically meaningful improvement" means improvement in patient conditions due to a drug and device combination treatment of the invention that does not occur when the same patient is treated with the same corticosteroid and dosage using a conventional nebulizer and previously used administration methods.

"MCID" means minimally clinically important difference.

"MMAD" means mass median aerodynamic diameter.

"Substantially" means at least 40% but is preferably more than 50%.

"Predominantly" means at least 50% but is preferably at least and above 75%.

BRIEF DESCRIPTION OF DRAWINGS

As seen in FIG. 4, median FEV1% of predicted values at the beginning of the treatment were 58.16% or 59.73% for both groups, respectively. After 18 weeks of treatment with full dose of budesonide, the median FEV1% of predicted of treated subjects improved by 17% to a value of 68.08%, with the net increase of forced expiratory volume being 205 ml. In contrast, the median FEV1% of predicted in the placebo group even decreased slightly by about 3% to a value of 57.85%.

Figure 8:
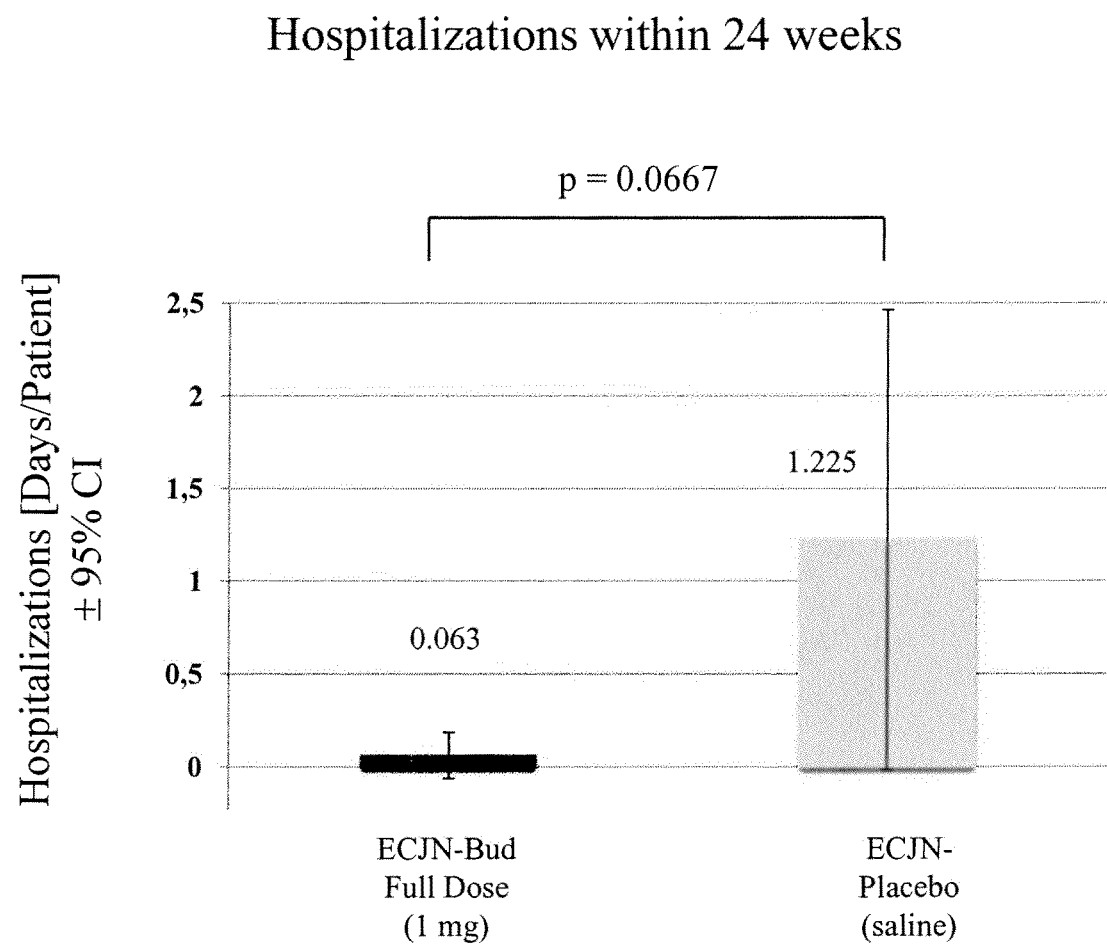

FIG. 8 illustrates the occurrence of hospitalizations expressed as days in the hospital per patient during the 24 week period following the treatment according to the invention. The patients treated with 1 mg of budesonide (ECJN-Bud/1 mg) spent only 0.063 days in 24 weeks in hospital, compared to patients receiving placebo, who spent 1.225 days in hospital during the same 24 week period (p=0.0667).

Figure 9:
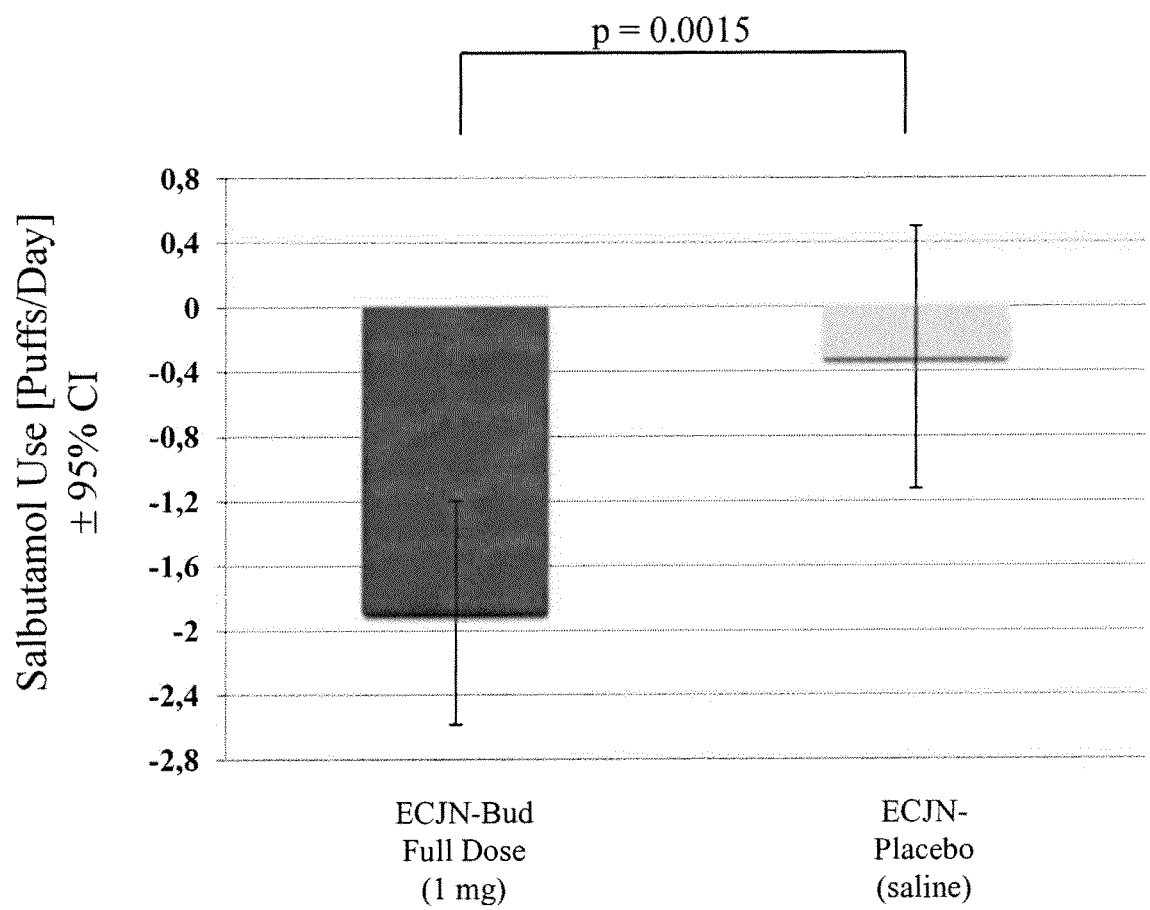

FIG. 9 graphically illustrates the reduction in use of salbutamol after 18 weeks treatment, expressed as puffs per day by patients treated with budesonide 1 mg (ECJN-Bud/1 mg) or placebo. As seen in FIG. 9, number of salbutamol puffs was significantly (p=0.0015) reduced with the full dose (ECJN-Bud/1 mg) budesonide treatment (−1.892 puffs/d) compared to placebo (−0.314 puffs, d).

Figure 10:
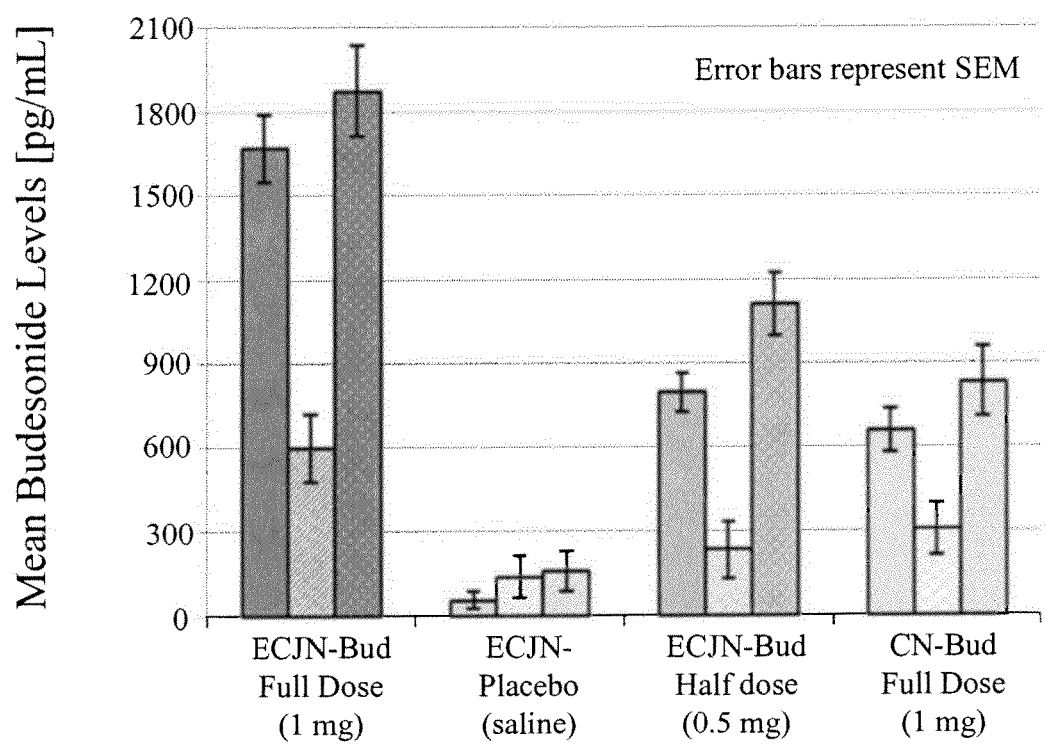

FIG. 10 shows the efficacy of the budesonide inhalation delivery determined by the levels of budesonide in the patient's serum before and after the inhalations in the four investigated groups (ECJN-Bud/1 mg; ECJN-Bud/0.5 mg; CN-Bud/1 mg and ECJN-Placebo). For budesonide serum concentration analysis, blood was drawn either before inhalation or 30-60 minutes following inhalation at baseline (post-inhalation) and at week 18 (pre- and post-inhalation). The three bars in FIG. 10 for each group denote levels at baseline (solid bar); levels at week 18, pre-inhalation (hatched bar); and levels at week 18, post-inhalation (dotted bar).

Figure 11:
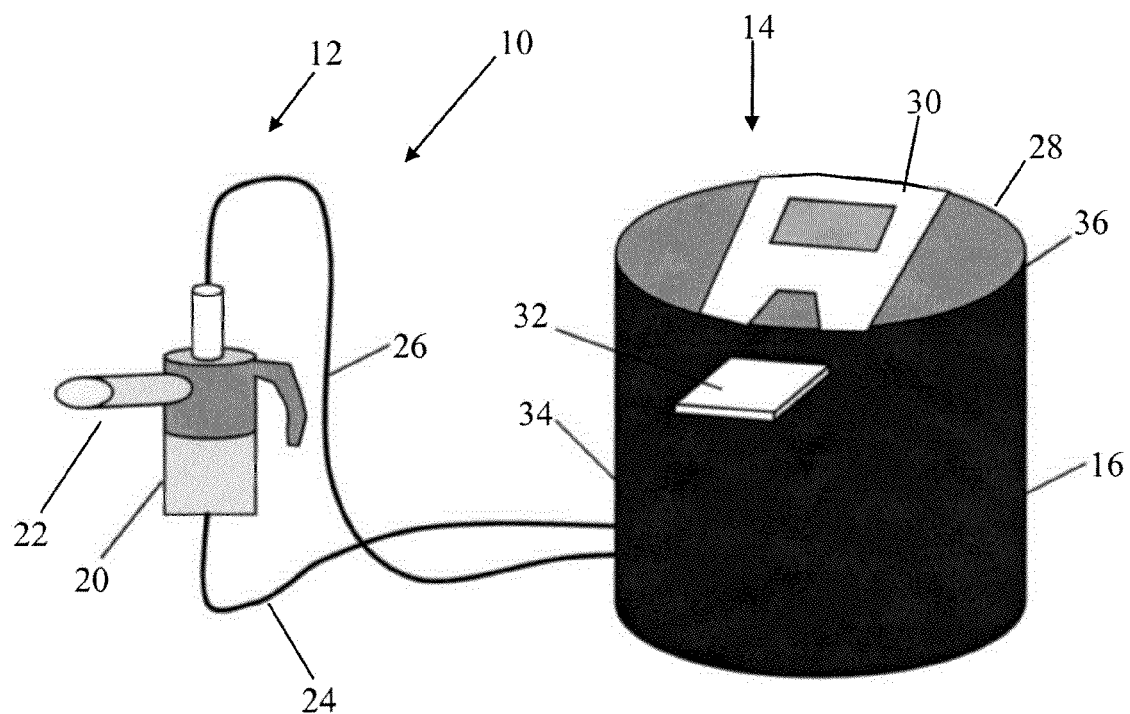

FIG. 11 shows one embodiment of the device of the invention. The device 10 comprises a jet nebulizer part 12 and a case for housing the air-flow control pump 28 and the compressor 36, and the electronic control part 14 comprising a display 30, and a therapeutic information protocol card 32.

Figure 12:
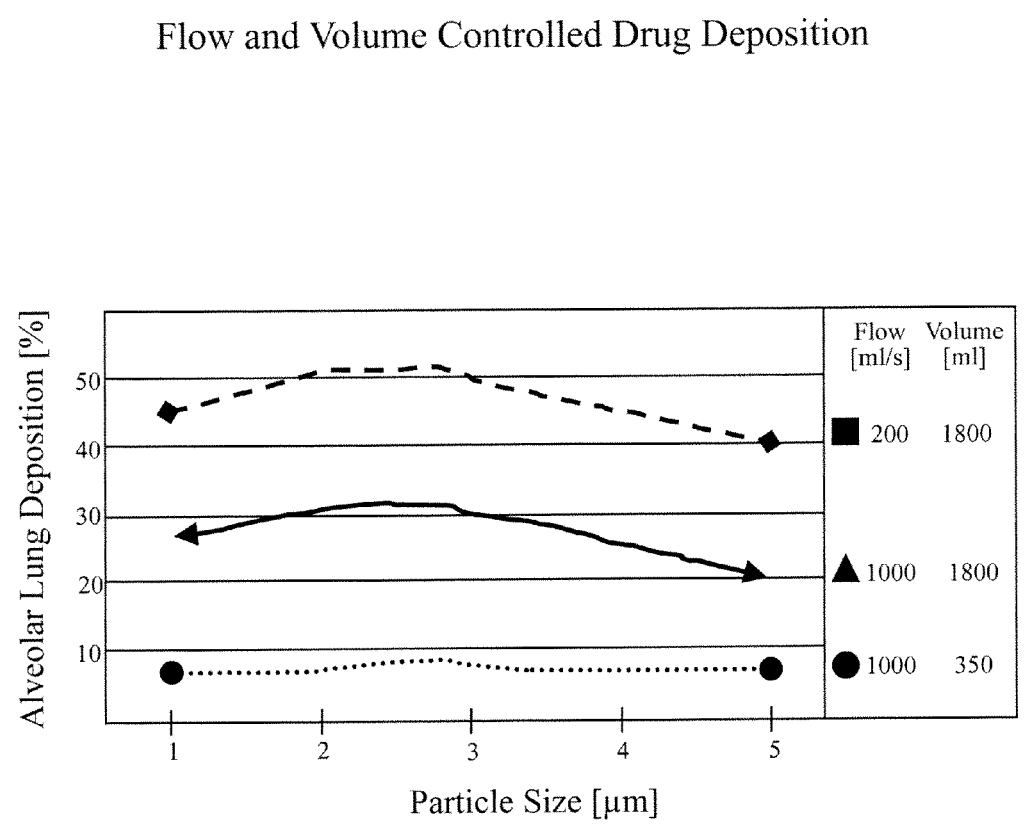

FIG. 12 shows dependency of the alveolar lung deposition of the aerosol having mean particle sizes between 1 and 5 μm at different exemplary flow rate and volume settings.

Figure 13A:
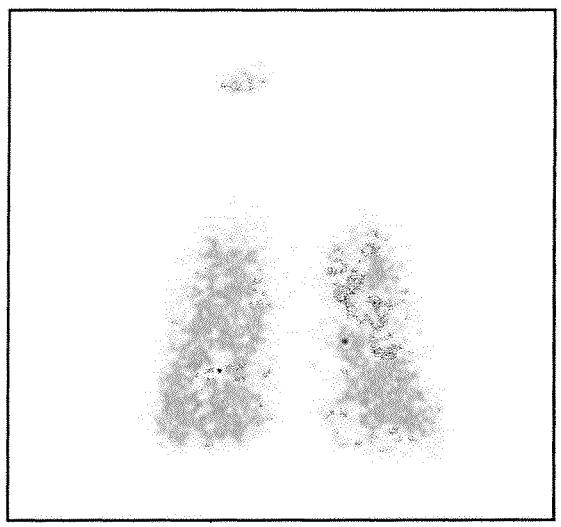
Figure 13B:
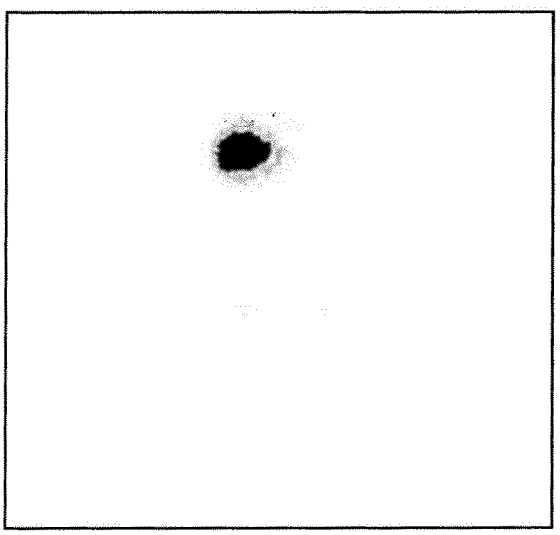

FIG. 13 is a depiction of deposited radioactivity to the lung (upon inhalation of radioactively labeled aerosol particles). The image is showing a drug deposition after flow and volume regulated inhalation (FIG. 13A) where the drug is deposited predominantly in the lungs periphery with only a small deposition seen in the oropharyngeal area compared to the drug deposition primarily in the oropharyngeal area with a very small deposition in the peripheral lungs following the unregulated inhalation (FIG. 13B).

DETAILED DESCRIPTION OF THE INVENTION

This invention concerns generally a drug and device combination system used in a method for inhalation therapy for treatment of severe and oral corticosteroid-dependent asthma and other respiratory diseases requiring a treatment with orally administered steroids. The inhalation therapy according to the invention results in the following benefits: complete weaning of more than 50% of all patients from oral corticosteroids; partial weaning to ≤50% of the initial oral corticosteroid dose in 80% of all patients treated with orally administered corticosteroid medication; substantial improvement in forced expiratory volume in one second (FEV1) achieved after 18 weeks of treatment; significant improvement of asthma Quality of Life measured by the Asthma Quality of Life Questionnaire(AQLQ); reduction of exacerbation of asthma symptoms; decrease in length and frequency of hospitalization of patients due to asthma episodes; and expectation of all these benefits to be achieved without any or with highly diminished secondary adversary reactions.

The Method

The method utilizes devices allowing the control and individualization of the flow rate and volume of the aerosol, optionally together with the application of an overpressure for severely asthmatic patients with a compromised breathing pattern. In this regard, the method comprises narrowly defined and controlled administration of the inhalable corticosteroid by a flow rate and volume regulated inhalation wherein the drug is administered predominantly into a target area of the lungs, in particular the small airways of the lungs, comprising terminal and respiratory bronchioles and alveolar ducts and sacs, by using a system comprising an inhalable corticosteroid drug and device combination.

The System

The system comprises a combination of an inhalable corticosteroid drug and an electronically controlled nebulizer device, such as a jet nebulizer, that regulates the aerosol's mean particle sizes as well as the flow rate and volume. The combination system permits a precise and fine tuning of the delivery of the inhalable drug into the lungs at an optimized flow rate and in an optimized volume to assure maximal homogeneous and reproducible peripheral deposition into the lung target area, with a minimal or nil deposition of the inhalable drug in the upper lungs, oropharyngeal or extrathoracic area.

The Inhalation Therapy

The inhalation therapy is individualized and programmable into a treatment protocol for the therapy design based on a patient's individual health conditions, as estimated from his/her FEV1 and FEV1% of predicted values. Depending on these values an appropriate inhalable corticosteroid and its required dose is chosen as well as an inhalation volume which will be tolerated by the individual patient. See further details on patient individualization below.

The Treatment Protocol

The individual treatment protocol is logged into each patient's therapeutic protocol card that is a part of the device. The protocol card is also used for a follow-up monitoring of compliance or non-compliance with such protocol. The individualized treatment protocol card comprises all relevant therapeutic parameters such as for example the date, onset and duration of each single inhalation treatment, the chosen inhalation volume setting and changes thereof, the number of breaths taken, data on whether each single inhalation treatment was finished successfully or was interrupted, whether the patient inhaled too fast, whether the pressure at the mouthpiece was too high or too low, whether treatments were missed, particularly with regard to bi-daily inhalation treatments, but also more technical information on the operation of the device such as error codes for certain events like "compressor damaged" or "wrong tubing attached".

The Device

The device of the invention is an electronically controlled inhalation system, such as a jet nebulizing system, modified to accommodate individualization of the treatment protocol and other features required for maximization of the treatment efficacy, accuracy, safety and reproducibility. The device of the invention automatically terminates therapy if and when the required dose is delivered by the required number of breaths and, therefore, overdosing is not possible. The safety of the device is further assured by the fact that due to its individual programming, wrong settings are not possible and every single inhalation volume delivers the same dose to the lungs. The electronically controlled inhalation system is seen in FIG. 11.

The Safety and Efficacy

The system, including a method and a treatment protocol, is safe, efficacious, reproducible, controllable, well tolerated by patients and individually programmable to assure a treatment safety and compliance. When the treatment protocol is followed, it results in very few side effects, in a very low number of asthma exacerbation episodes, and it improves the Quality of Life of patients and reduces occurrences and length of hospitalizations. The device's capability to control and regulate flow rate and inhalation volume regulating assures dose reproducibility and maximized, homogeneous delivery of the inhalable drug directly to the target areas of the lower lungs. Furthermore, this decreases the deposition of inhalable corticosteroids in the upper lungs and the oropharyngeal area and thereby reduces the drug dose requirement, drug waste and undesirable side effects.

Improvements in Asthma and Respiratory Diseases

The method of the invention results in complete or partial weaning of a patient from orally administered steroids and in an unexpectedly large improvement of pulmonary function, improvement in Quality of Life in asthmatic patients, unexpected and substantial reduction of symptoms exacerbations, reduction in frequency and lengths of hospitalizations and in recovery of endogenous cortisol production.

The Inhalable Corticosteroid Drugs

The inhalable corticosteroid drug is selected from the group consisting of budesonide, fluticasone, beclomethasone dipropionate, mometasone furoate, ciclesonide, flunisolide and triamcinolone acetonide. It is intended that also included are any other inhalable corticosteroids that are or may be currently available, may be in development or may become available in the future.

Budesonide as a Representative Inhalable Corticosteroid

Budesonide was selected as a representative inhalable corticosteroid in the following clinical studies performed in order to develop an efficacious drug and device combination system for weaning patients from orally administered corticosteroids. The system comprises a drug and device combination, a method and a protocol for treatment of severe asthma and other oral corticosteroid-dependent respiratory diseases. Aim of these studies was to provide a system that would result in a safe and well tolerated complete weaning of patients from the orally administered steroids or in a safe and well tolerated partial weaning to at least 50%, preferably less than 50% of the initial oral corticosteroid dose, for those patients still requiring a concomitant oral administration of corticosteroid. As described below, when the protocol of the invention is followed, the administration of budesonide (1 mg or 0.5 mg) in a twice a day regimen was sufficient to achieve these aims.

With exception of dose adjustments, budesonide may be replaced with every other inhalable corticosteroid such as fluticasone, beclomethasone dipropionate, mometasone furoate, ciclesonide, flunisolide, triamcinolone acetonide and any other corticosteroid currently available or becoming available in the future. All these corticosteroids are suitable to be used in the system and the method of the invention.

For clinical studies, the budesonide was administered to severely asthmatic patients with oral corticosteroid-dependency who were until then treated with oral corticosteroids. The clinical studies were multi-center, double-blind, randomized and placebo-controlled. Budesonide was prepared and added to the nebulizer in a 2 ml filling dose. 199 patients with severe asthma classified as Gina V stage, between 18 and 65 years old, treated regularly with oral corticosteroids, were subject of this clinical trial of which 80 patients were treated with budesonide full dose (ECJN-Bud/1 mg), 39 patients were treated with budesonide half dose (ECJN-Bud/0.5 mg), 40 patients were controls treated with placebo (2 ml saline), with all three above treatments using the electronically controlled jet nebulizer, and 40 patients were treated with budesonide full dose using a conventional PARI® LC nebulizer (CN-Bud/1 mg). All subjects were patients suffering from severe asthma treated prior to the clinical trial for at least 6 months with oral corticosteroids in dosages from 5 mg to 40 mg per day.

Budesonide was administered twice daily (BID) in 1 mg/2 ml or 0.5 mg/2 ml filling doses (based on saline solution) administered either with the electronically controlled jet nebulizer (ECJN-Bud) or in only the 1 mg/2 ml filling dose with the conventional PARI® nebulizer (CN-Bud). Saline (0.9%; 2 ml) was used as a control placebo medication and administered as 2 ml solution twice a day to a control group of patients with the electronically controlled jet nebulizer (ECJN-Placebo). The filing dose (2 ml) of the budesonide solution containing either 1 mg or 0.5 mg of budesonide was placed into the container of the nebulizer. The solution was administered as an aerosol having a mean particle size predominantly in the range from 1 to about 5 µm, preferably between 3 and 4 µm and most preferably about 3.8 µm (MMAD) using the electronically controlled jet nebulizer for a flow rate and volume controlled inhalation or the conventional PARI nebulizer (CN-Bud) without such control. The clinical trial lasted 18 weeks including the therapy and oral corticosteroid tapering, followed by post clinical trial monitoring.

In terms of weaning patients from the oral corticosteroids, results of this clinical study shows that there was complete weaning from orally administered corticosteroids in more than 50% of all treated patients and there was partial weaning to ≤50% of the initial oral corticosteroid dose in about 80% of all treated patients. In other words, following the treatment protocol with the full budesonide dose (ECJN-Bud/1 mg), more than 50% of all patients were completely weaned from oral corticosteroids after 18 weeks of treatment. Additionally, 80% of all treated patients were weaned to at least 50% or less of their initial daily dose of oral corticosteroid.

Complete Weaning from Oral Corticosteroids in Asthmatic Patients

Patients diagnosed with asthma, particularly with severe and oral corticosteroid-dependent asthma requiring treatment with orally administered corticosteroid are completely weaned from oral corticosteroids in more than 50% of all cases, specifically 56.3%, when subjected to inhalation therapy using the drug and device combination system and a method according to the invention. Results are seen in FIG. 1 and Table 1

Figure 1:
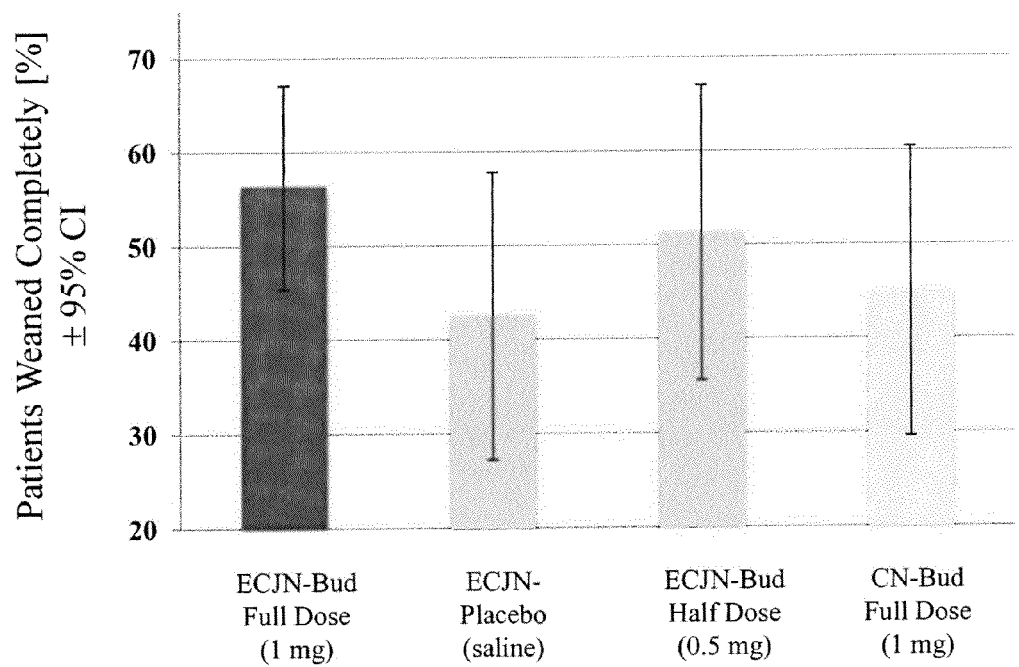
FIG. 1 illustrates complete weaning of oral corticosteroid-dependent patients from treatment with orally administered budesonide. Patients treated according to the invention with full dose of budesonide (ECJN-Bud/1 mg) administered with the electronically controlled jet nebulizer are completely weaned from the oral corticosteroids in 56.3% of the cases. Treatment of patients with a half-dose of budesonide (ECJN-Bud/0.5 mg) also resulted in over 51.3% of patients completely weaned. In comparison, only 42.5% of patients were completely weaned with the placebo (saline 2 ml) when administered with the electronically controlled jet nebulizer and only 45% with the full dose of budesonide (CN-Bud/1 mg) administered with the conventional PAR I® nebulizer.

FIG. 1 shows the percentages of patients completely weaned from oral corticosteroids at week 18 after receiving either the full drug dose (ECJN-Bud/1 mg) of budesonide administered by the electronically controlled jet nebulizer, placebo administered by electronically controlled jet nebulizer, the half dose (ECJN-Bud/0.5 mg) of budesonide administered by the electronically controlled jet nebulizer, or the full dose of budesonide administered with a conventional PARI nebulizer (CN-Bud/1 mg). These data are further summarized and shown in more detail in Table 1.

TABLE 1

Subjects Fully Weaned From Oral Corticosteroids at Week 18

|  | ECJN-Bud 1 mg N = 80 | | ECJN-Placebo N = 40 | | ECJN-Bud 0.5 mg N = 39 | | CN-Bud 1 mg N = 40 | |
| --- | --- | --- | --- | --- | --- | --- | --- | --- |
| N | n | % | n | % | n | % | n | % |
| Fully Weaned Off | 45 | 56.3 | 17 | 42.5 | 20 | 51.3 | 18 | 45.0 |
| Not Fully Weaned Off | 32 | 40.0 | 23 | 57.5 | 18 | 46.2 | 21 | 52.5 |
| Not Decisive | 3 | 3.8 | 0 | 0.0 | 1 | 2.6 | 1 | 2.5 |

ECJN-Bud = Inhalable Budesonide delivered by the electronically controlled jet nebulizer;
ECJN-Placebo = Saline administered by the electronically controlled jet nebulizer;
CN-Bud = Budesonide delivered by the conventional PARI nebulizer As seen from FIG. 1 and Table 1, more than 50%, specifically 56.3%, of all patients in the ECJN-Bud/1 mg group, and 51.3% in the ECJN-Bud/0.5 mg group were completely weaned from oral corticosteroids. In the CN-Bud/1 mg group, only 45% of subjects were weaned completely from oral corticosteroids, i.e. a weaning percentage only slightly higher than in the placebo group at 42.5%; clearly confirming the inefficacy of the currently available treatment with conventional nebulizers. The advantage of the electronically controlled jet nebulizer system over the conventional PARI nebulizer used in the drug-device combination system of the invention for complete weaning from OCS is therefore clearly established.

Additionally, improvements in overall physical conditions and functions of the lungs, such as improvement of FEV1, AQLQ, exacerbation of asthma, number and length of hospitalization, and side effects, as further described below, were observed in subjects fully weaned from oral corticosteroids.

Partial Weaning from Oral Corticosteroids in Asthmatic Patient

Patients diagnosed with severe and oral corticosteroid-dependent asthma requiring a treatment with orally administered corticosteroids show a reduction by at least 50% or more in their initial daily dose of oral corticosteroids in about 80% of all cases, when subjected to inhalation therapy using the drug and device combination system according to the invention. These results show that the dosage of oral corticosteroids which is still required by such partially weaned patients that is concomitant to the inhalation therapy according to the invention, is smaller or equal to 50% of their initial dose. Note that by definition the group of partially weaned patients includes the group of completely weaned patients.

Figure 2:
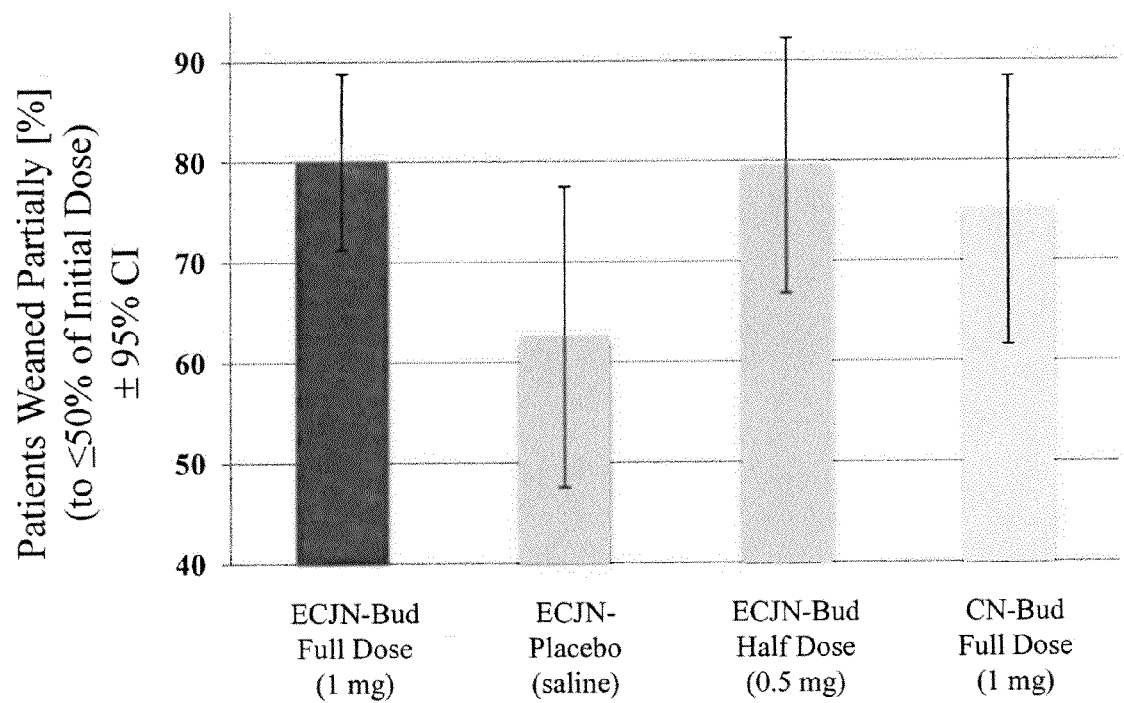
FIG. 2 shows a percentage of patients partially weaned from oral corticosteroids to ≤50% of the initial dose when treated with either the full budesonide dose (ECJN-Bud/1 mg) by electronically controlled jet nebulizer, or placebo (saline 2 ml) administered by said electronically controlled jet nebulizer, or a half-dose of budesonide (ECJN-Bud/0.5 mg) administered by the electronically controlled jet nebulizer, or a full dose of budesonide administered with the conventional PARI® nebulizer (CN-Bud/1 mg). Such partial weaning occurred in 80% of all subjects treated with the full budesonide dose (ECJN-Bud/1 mg) as well as in about 79% of all subjects treated with the half dose of budesonide (ECJN-Bud/0.5 mg) administered with the electronically controlled jet nebulizer system configured according to the invention, compared to only about 63% for placebo (p<0.05) or about 75% of subjects treated with the full dose of budesonide administered by the conventional PARI nebulizer (CN-Bud/1 mg).

FIG. 2 shows percentages of patients partially weaned from oral corticosteroids, comparing the full dose (ECJN-Bud/1 mg) of budesonide to placebo (saline 2 ml) and to half dose (ECJN-Bud/0.5 mg) of budesonide, all three administered by the same electronically controlled jet nebulizer, as well as to the full dose of budesonide administered with the conventional PARI nebulizer (CN-Bud/1 mg).

As seen in FIG. 2, such partial weaning occurred in 80% of all subjects treated with the full budesonide dose (ECJN-Bud/1 mg) and also about 79.5% of all subjects treated with the half dose of budesonide (ECJN-Bud/0.5 mg), compared to only about 62.5% for placebo (p<0.05) and compared to about 75% of subjects treated with the full dose of budesonide administered by the conventional PARI nebulizer (CN-Bud/1 mg). The results clearly show the superiority of the drug-device combination of the invention over the conventional nebulizer administration where the both full and half dosage of budesonide administered according to the invention achieve 5%, or almost 5% in case of the half dosage of budesonide, reduction in the initial corticosteroid dosage needed by asthma patients. These results can also be seen in further detail in Table 2.

TABLE 2

Subjects Partially Weaned From Oral Corticosteroids at Week 18
(Reduction to ≤50% of the Initial Oral Corticosteroid Dose)

|  | ECJN-Bud 1 mg N = 80 | | ECJN-Placebo N = 40 | | ECJN-Bud 0.5 mg N = 39 | | CN-Bud 1 mg N = 40 | |
| --- | --- | --- | --- | --- | --- | --- | --- | --- |
| N | n | % | n | % | n | % | n | % |
| Partially Weaned | 64 | 80.0 | 25 | 62.5 | 31 | 79.5 | 30 | 75.0 |
| Not weaned to ≤50% of initial dose | 9 | 11.3 | 10 | 25.0 | 3 | 7.7 | 4 | 10.0 |
| Excluded | 4 | 5.0 | 5 | 12.5 | 4 | 10.3 | 5 | 12.5 |
| Not Decisive | 3 | 3.8 | 0 | 0.0 | 1 | 2.6 | 1 | 2.5 |

Figure 3:
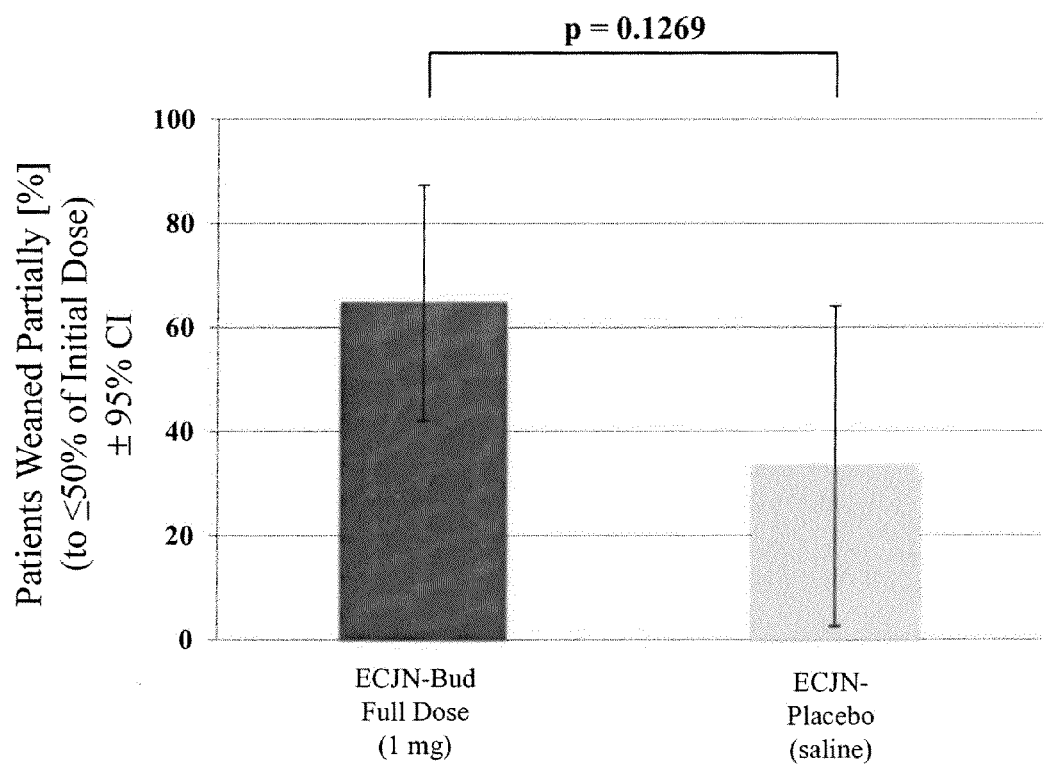
FIG. 3 shows the results of the study presented in FIG. 2 for the subgroup of subjects treated with an initial dose of oral budesonide larger than 10 mg. The same budesonide full dose (ECJN-Bud/1 mg) treatment was used in this subgroup and was compared to placebo (saline 2 ml). About 65% of these patients weaned to ≤50% of their initial dose, compared to about 33% in the placebo group (p=01.269).

These results were further analyzed for the subgroup of subjects initially treated with an oral corticosteroid dose larger than 10 mg/day. The results are seen in FIG. 3. This analysis was conducted as it was anticipated that patients requiring higher initial doses of oral corticosteroids, that is those patients having more severe form of and being more affected by asthma, would react stronger when reducing their oral corticosteroid doses. Indeed, only 33.3% of patients in the ECJN-Placebo subgroup with initial OCS dose >10 mg could be partially weaned, compared to the above mentioned 62.5% of all placebo-treated patients regardless of their initial dose (see FIG. 2 and Table 2). This indicates that in the more severely affected subgroup receiving >10 mg OCS/day substitution of oral corticosteroids with mere saline inhalation would not sufficiently stabilize asthma conditions as it is required for weaning according to this invention. However, in the ECJN-Bud/1 mg subgroup treated with initial OCS dose >10 mg, still 64.7% of patients could be partially weaned from oral corticosteroids, as compared to only 33.3% of the placebo group. These results further confirm efficacy of the drug-device combination treatment even for severely affected patients.

Improvements in overall physical conditions and functions of the lungs, such as improvement of FEV1, AQLQ, exacerbation of asthma, number and length of hospitalization, and side effects, as described below, were observed in subjects partially weaned from oral corticosteroids.

FEV1 Improvement in Treated Asthmatic Patients

Functionality of the lungs, determined by forced expiratory volume in one second (FEV1), is improved significantly with about 17% increase observed for the median value FEV1% of predicted after 18 weeks of treatment with full dose (1 mg) of budesonide, using the drug and device combination system of the invention.

Figure 4:
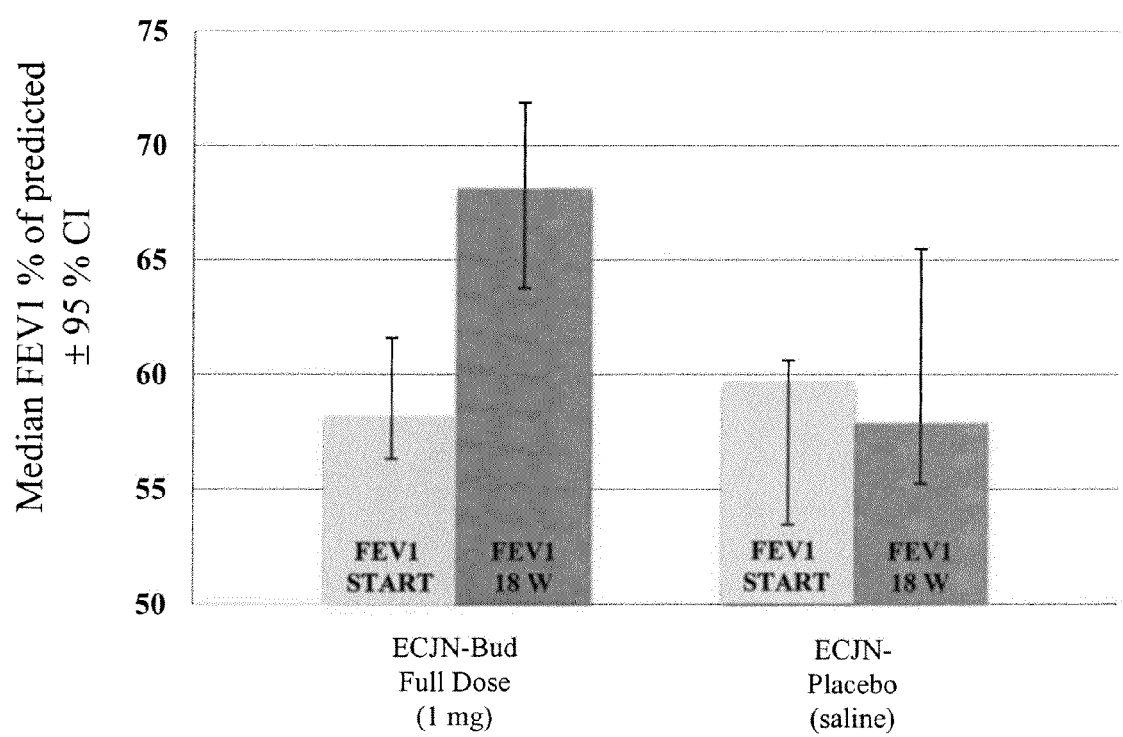
FIG. 4 shows comparative results of the median forced expiratory volume in one second (FEV1), expressed here as the percentage based on the predicted average FEV1 for persons of similar height, age and sex (FEV1% of predicted), in terms of improvement from the beginning of the study until after 18 weeks of treatment of subjects with either a full dose of budesonide (ECJN-Bud/1 mg) or placebo (saline 2 ml), both administered with the electronically controlled jet nebulizer.

FIG. 4 shows the median forced expiratory volume in one second—expressed here as the percentage based on the predicted average FEV1 for persons of similar height, age and sex (FEV1% of predicted), at the start of the study and after 18 weeks for subjects treated with either a full dose of budesonide (ECJN-Bud/1 mg) or placebo (saline 2 ml), both administered with the electronically controlled jet nebulizer system. As seen in FIG. 4, median values at the beginning of the treatment were 58.16% or 59.73% for the two groups, respectively. After 18 weeks, the median values of subjects treated with a full dose of budesonide improved by about 17% to a value of 68.08%, with the net FEV1 increase being 205 ml. In contrast, the values in the placebo group even decreased slightly by about 3% to a value of 57.85%.

Figure 5:
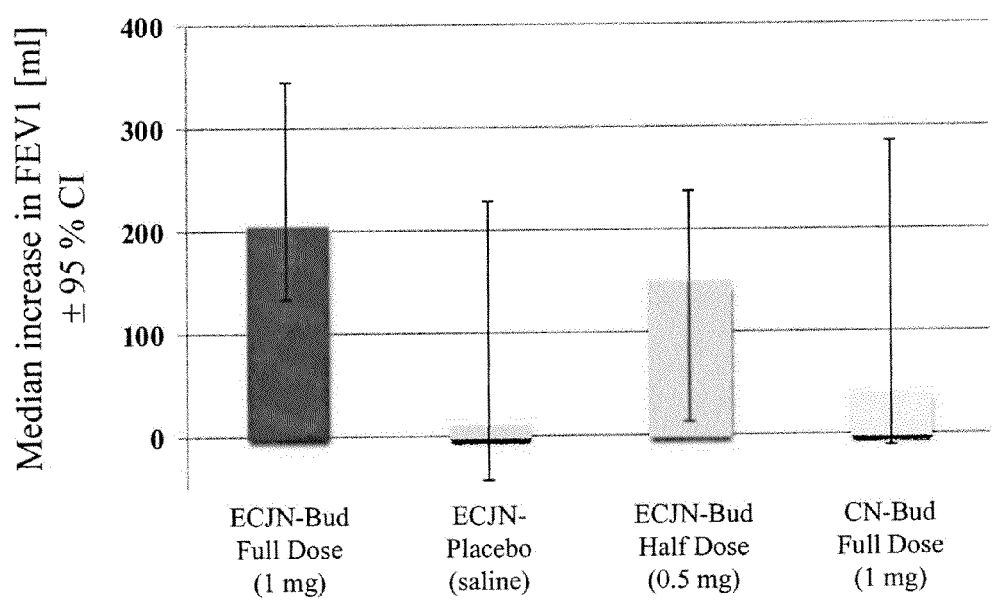
FIG. 5 shows the results from the same study expressed as median FEV1 values in ml for all four groups, i.e., subjects treated either with a full dose (EON-Bud/1 mg) or a half dose of budesonide (ECJN-Bud/0.5 mg) or with 2 ml saline (ECJN-Placebo), all three administered with the electronically controlled jet nebulizer, or with the full dose of budesonide administered by the conventional PARI nebulizer (CN-Bud/1 mg). The results show that the full dose of budesonide administered with the electronically controlled jet nebulizer (ECJN-Bud/1 mg) resulted in 205 ml increase of median FEV1 compared to only 10 ml with placebo, 150 ml with the half dose of budesonide (ECJN-Bud/0.5 mg) and only 40 ml with the full budesonide dose administered by conventional PARI nebulizer (CN-Bud/1 mg).

FIG. 5 shows the results from the same study expressed as median FEV1 values in ml for all four groups. After 18 weeks of treatment, median FEV1 in the ECJN-Bud/1 mg group increased by 205 ml compared to only 10 ml for the placebo group. The ECJN-Bud/0.5 mg group achieved an increase of around 150 ml and the CN-Bud/1 mg group an increase of only 40 ml. Clearly, the combination of the full budesonide dose and the electronically controlled jet nebulizing device used in the method of the invention is far superior to any other dose and route of delivery or placebo. Additionally, the half budesonide dosage administered with the drug-device combination still shows substantial improvement of FEV1 over both the placebo and also over the full dosage of budesonide administered with the conventional nebulizer.

Table 3 presents the results of the FEV1 improvement depicted in FIG. 5 after 18 weeks of treatment in more detail. The values in table 3 show the percent change of the FEV1 values of all patient (in mL), expressed as the respective mean and median values.

TABLE 3

Percent Change in FEV1 (ml) from Baseline to Week 18

[%]

|  | ECJN-Bud 1 mg N = 76 | ECJN-Placebo N = 39 | ECJN-Bud 0.5 mg N = 39 | CN-Bud 1 mg N = 39 |
|---|---|---|---|---|
| Mean ± SD | 16.49 ± 30.33 | 6.24 ± 24.56 | 9.50 ± 20.66 | 8.64 ± 27.83 |
| 95% Confidence Interval | 9.56; 23.42 | −1.72; 14.20 | 2.81; 16.20 | −0.38; 17.66 |
| Median | 12.97 | 0.58 | 10.78 | 2.60 |

ECJN-Bud = Inhalable Budesonide administered by the electronically controlled jet nebulizer; ECJN-Placebo = Saline administered by the electronically controlled jet nebulizer; CN-Bud = Budesonide administered by PARI conventional nebulizer Results seen in FIGS. 4 and 5 and in Table 3 show that there is a large improvement in FEV1 in subjects treated with the full 1 mg dose of budesonide using the system and method of the invention. Placebo does not show substantial improvements of the median percent increase of FEV1 (only 0.58%), compared to almost 13% improvement in the full dose budesonide group treated with the electronically controlled inhalation system (p=0.0707). The group which received the same 1 mg dose of budesonide via the conventional nebulizer, on the other hand, achieved only a minor median percent increase of FEV1 of 2.60%. Remarkably, even the group treated with only half the dose of budesonide, administered by the electronically controlled inhalation system (ECJN-Bud/0.5 mg) showed a larger median percent increase in FEV1 (10.78%) than placebo and/or CN-Bud/1 mg group, indicating the higher efficacy of the budesonide treatment according to the invention. Such improvements of FEV1 in patients with severe asthma requiring constant OCS therapy represent a very important and clinically meaningful result. These results again confirm that the instant drug and device combination system used in the method for treatment of severe asthma and other respiratory disease is far superior to any other currently existing method for treatment of severe oral corticosteroid-dependent asthma and results in unexpected improvements.

Quality of Life Improvement in Treated Asthmatic Patients

Following the treatment with drug and device combination system of the invention, Quality of Life in asthmatic patients, determined by Asthmatic Quality of Life Questionnaire (AQLQ) is improved significantly by 0.83 score points which is clearly above the minimally clinically important difference (MCID) of 0.5 points.

Quality of Life (QoL) of subjects treated according to the invention was assessed via the validated Mini Asthma Quality of Life Questionnaire (MiniAQLQ), which focuses on asthma symptoms that affect subject's Quality of Life. It contains 15 questions which are divided into different domains, representing different potential impairments patients with asthma typically report (i.e., symptoms, activity limitation, emotional function and environmental stimuli).

Figure 6:
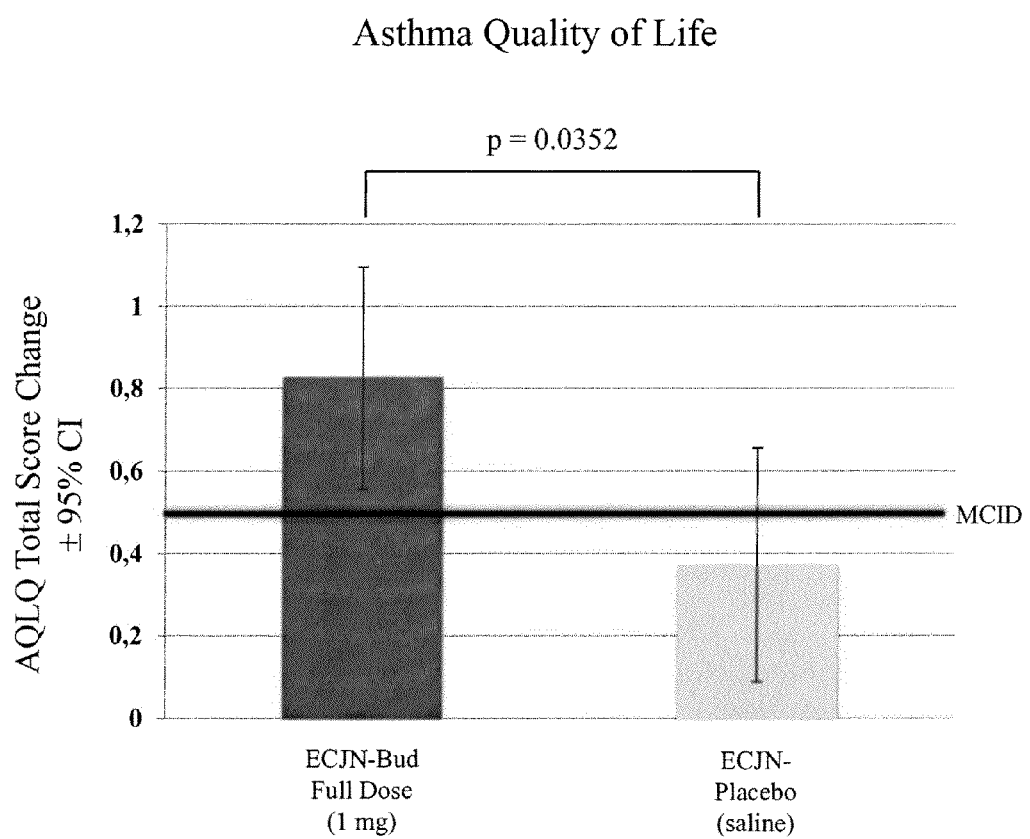
FIG. 6 shows improvement in Quality of Life (QoL) of subject treated according to the invention assessed with Mini Asthma Quality of Life Questionnaire (MiniAQLQ). When the AQLQ total score was determined in subjects with complete weaning from OCS treated with full dose of budesonide (ECJN-Bud/1 mg) and compared to AQLQ total score change in subject treated with placebo, there was significant (p=0.0352) improvement in Quality of Life in budesonide treated patients. Such improvement was expressed as a total score above or under the minimal clinically important difference (MCID) set to be 0.5. Inhalation of the full dose budesonide (1 mg) improved mean AQLQ well above MCID (0.826) while the inhalation of the placebo did not (0.372).

When the AQLQ total score was determined in subjects with complete weaning from OCS treated with full dose of budesonide and compared to placebo, there was a significant (P=0.0352) improvement in Quality of Life in budesonide treated patients. Such improvement was expressed as a total score above or under the minimal clinically important difference (MCID) set to be 0.5. As seen in FIG. 6, inhalation of full dose budesonide (ECJN-Bud/1 mg) improved mean AQLQ well above MCID (0.826) while the placebo did not (0.372).

Based on the results above, clearly the Quality of Life in severe asthma subjects treated with 1 mg of inhalable budesonide according to the invention was improved and these subjects experienced such clinically meaningful improvements in QoL even and particularly when reducing oral corticosteroids and replacing them with the improved budesonide inhalation according to the invention. QoL improvement also included improved and increased FEV1 and reduced usage of emergency medication, such as for example salbutamol.

Exacerbation of Asthma Symptom in Treated Subjects

Figure 7:
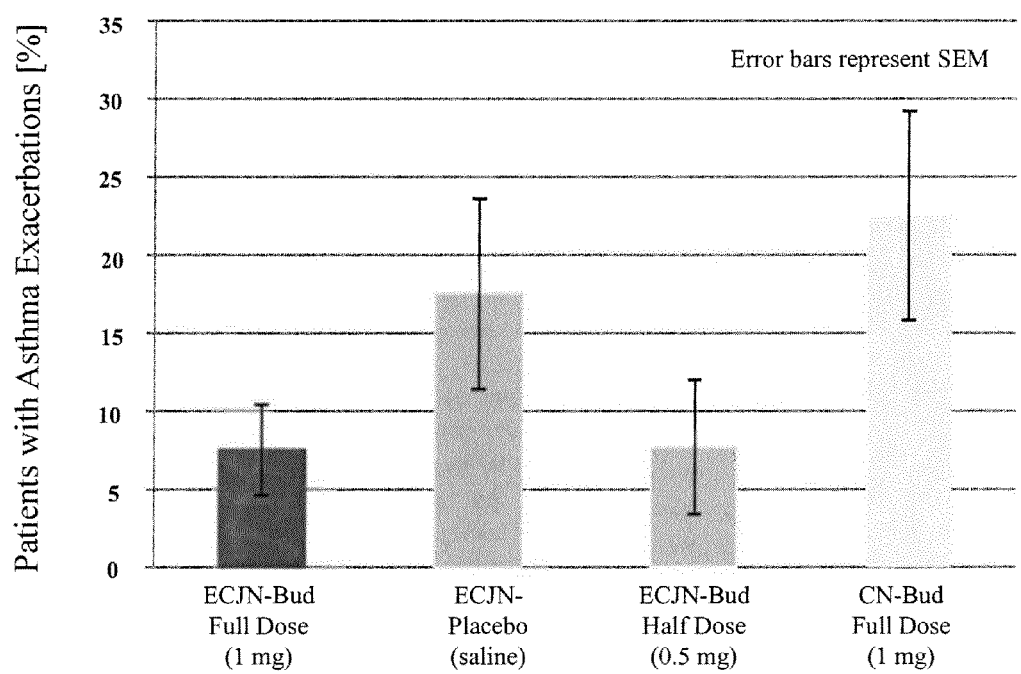
FIG. 7 shows the occurrence of asthma exacerbations. Exacerbation of asthmatic conditions is experienced by only 7.5% and 7.7% of patients treated with the full (ECJN-Bud/1 mg) and the half dose of budesonide (ECJN-Bud/0.5 mg), respectively, compared to 17.5% of patients in the placebo control group, all three administered with the electronically controlled jet nebulizer. Interestingly, even 22.5% of the subjects treated with the full dose budesonide, administered with the conventional PARI nebulizer (CN-Bud/1 mg), experienced asthma exacerbations, i.e. slightly more than the placebo group; indicating the limitations and inefficiency of the conventional budesonide treatment.

The occurrence of exacerbations of asthmatic conditions is reduced to 7.5% and 7.7% of all cases, respectively, for the subjects treated with full and half dose of budesonide (ECJN-Bud/1 and 0.5 mg) compared to 17.5% of all subjects experiencing exacerbations in the placebo control group and even 22.5% in the group treated with the conventional nebulizer (CN-Bud/1 mg) as seen in FIG. 7. These results demonstrate and confirm that the drug and device combination system of the invention utilizing the electronically controlled jet nebulizing system for delivery of the inhalable corticosteroid results in unexpectedly low asthma exacerbations when compared to the inhalable corticosteroid administered with the conventional PARI nebulizer and when compared to the control receiving placebo using the electronically controlled jet nebulizing system. The fact that asthma exacerbations were similarly frequent in the placebo and the CN-Bud/1 mg groups further highlights the inefficacy of the conventional budesonide treatment.

The results of the exacerbation study are shown in more detail in Table 4.

TABLE 4

Asthma Exacerbations

|  | ECJN-Bud 1 mg | | ECJN-Placebo | | ECJN-Bud 0.5 mg | | CN-Bud 1 mg | |
|---|---|---|---|---|---|---|---|---|
|  | n | % | n | % | n | % | n | % |
| Full Analysis Set |  | 80 |  | 40 |  | 39 |  | 40 |
| At Least One Exacerbation | 6 | 7.5 | 7 | 17.5 | 3 | 7.7 | 9 | 22.5 |
| No Exacerbation | 74 | 92.5 | 33 | 82.5 | 36 | 92.3 | 31 | 77.5 |

TABLE 4-continued

Asthma Exacerbations

|  | ECJN-Bud 1 mg | | ECJN-Placebo | | ECJN-Bud 0.5 mg | | CN-Bud 1 mg | |
|---|---|---|---|---|---|---|---|---|
|  | n | % | n | % | n | % | n | % |
| Subgroup Initial OCS dose 5-10 mg | 63 | | 31 | | 32 | | 30 | |
| At Least One Exacerbation | 4 | 6.3 | 3 | 9.7 | 2 | 6.3 | 6 | 20.0 |
| No Exacerbation | 59 | 93.7 | 28 | 90.3 | 30 | 93.8 | 24 | 80.0 |
| Subgroup Initial OCS dose 10-40 mg | 17 | | 9 | | 7 | | 10 | |
| At Least One Exacerbation | 2 | 11.8 | 4 | 44.4 | 1 | 14.3 | 3 | 30.0 |
| No Exacerbation | 15 | 88.2 | 5 | 55.6 | 6 | 85.7 | 7 | 70.0 |

ECJN-Bud = Inhalable Budesonide administered by the electronically controlled jet nebulizer;
ECJN-Placebo = Saline administered by the electronically controlled jet nebulizer;
CN-Bud = Budesonide administered by PARI conventional nebulizer Moreover, the difference in exacerbation rate is even more evident when the more severely impaired subgroup of patients receiving an initial oral corticosteroid dose larger than 10 mg/day and up to 40 mg/day. In this subgroup, only 11.8% of subjects treated with the full dose of budesonide (1 mg) and only 14.3% of subjects treated with the half dose (0.5 mg) experienced at least one exacerbation, compared to 44.4% in the placebo group or 30.0% in the CN-Bud/1 mg group. The latter subjects, in particular, cannot be weaned safely from OCS.

The subgroup of patients initially requiring 5 to 10 mg/day of oral corticosteroids also showed lower numbers of exacerbations in the ECJN-Bud/1 mg and the ECJN-Bud/0.5 mg group (6.3% experiencing at least one exacerbation) compared to 9.7% of exacerbations in the placebo group and 20% exacerbation in the CN-Bud/1 mg group.

Hospitalization in Treated Asthmatic Patients

Severe oral corticosteroid-dependent asthma often results in asthma exacerbations requiring hospitalization and urgent care. Treatment of the asthma patients with the system and method of the invention results in pronounced reduction in asthma exacerbation episodes and fewer hospitalizations. Patients with oral corticosteroid-dependent asthma treated with the full dose of 1 mg of inhalable budesonide according to the invention were followed for 24 weeks and their hospitalizations were recorded. Results are seen in FIG. 8 where the hospitalization are expressed as days in the hospital per patient during the 24 week period. As seen from FIG. 8, the patients treated with 1 mg of budesonide (ECJN-Bud/1 mg) spent only 0.063 days in 24 days compared to patients receiving placebo, who spent 1.225 days in the hospital during the same 24 week period. Consequently, there was a more than 20 times, significant reduction in the number of hospitalizations (p=0.0667) for patients treated according to the method of the invention with the drug-device combination system.

Table 5 shows the number of days of hospitalization for each treatment group. Seven subjects out of the total 198 studied subjects reported hospitalizations due to asthma. The numbers of days in hospital ranged between 5 and 17.

TABLE 5

Hospitalization due to Asthma

|  | ECJN-Bud 1 mg N = 80 | | ECJN-Placebo N = 40 | | ECJN-Bud 0.5 mg N = 39 | | CN-Bud 1 mg N = 40 | |
|---|---|---|---|---|---|---|---|---|
|  | n | % | n | % | n | % | n | % |
| Subjects with Hospitalization due to Asthma | 1 | 1.3 | 4 | 10.0 | 1 | 2.6 | 1 | 2.5 |

ECJN-Bud = Inhalable Budesonide administered by the electronically controlled jet nebulizer;
ECJN-Placebo = Saline administered by the electronically controlled jet nebulizer;
CN-Bud = Budesonide administered by PARI conventional nebulizer Four subjects (10%) from the placebo group required between 9 and 17 days of hospitalization. In comparison, only one subject in each group treated with budesonide required hospitalization of 5 days; i.e. percentagewise, only 1.3% of subjects from the ECJN-Bud/1 mg group and 2.6% and 2.5% subjects of the ECJN-Bud/0.5 mg and the CN-Bud/1 mg groups, respectively. These results clearly show the advantages of treatment of patients with severe oral corticosteroid-dependent asthma achieved with the method and drug and device combination system of the invention.

Reduction in Bronchodilators Use

Bronchospasm, one of the severe asthma exacerbation symptoms, is typically treated with bronchodilators, of which the most preferably used is salbutamol. Salbutamol also known as albuterol belongs to the family of drugs known as adrenergic bronchodilators used to open up the bronchial tubes passages) in the lungs during bronchospasm caused by asthma.

FIG. 9 graphically illustrates the reduction in use of salbutamol after 18 weeks treatment, expressed as puffs per day by patients treated with either the full dose of budesonide (ECJN-Bud/1 mg) or placebo. As seen in FIG. 9, after 18 weeks the number of salbutamol puffs was significantly (p=0.0015) reduced under full dose budesonide treatment (−1.892 puffs/d) compared to placebo (−0.314 puffs/d). The change in the number of salbutamol puffs per day from baseline to week 18 was calculated based on the data from the patients' diaries concerning rescue bronchodilator puffs. In line with the improved exacerbation rate and improvements in FEV1, these results further support findings that the use of 1 mg inhalable budesonide according to the invention results in safe and well tolerated oral corticosteroids reduction as indicated by a significant decrease in need of bronchodilators as an emergency medication in a patient population suffering from severe asthma.

Decrease or Elimination of Secondary Side Effects in Treated Asthmatic Patients

Treatment of severe oral corticosteroid-dependent asthma according to the invention has also an effect on the occurrence and severity of side effects typically observed with inhalable corticosteroids. Typically, when the corticosteroid is delivered by inhalation, a certain portion of the corticosteroid is deposited in oropharyngeal and/or extrathoracic area including mouth, nose, throat, pharynx and larynx. Any deposition of the inhalable corticosteroid in these areas is undesirable and leads to development of adverse effect such as hoarseness, dysphonia, loss of voice, laryngitis and candidiasis. For these reasons, it is preferable that there is no or only a very small residual deposition in the mouth, nose, throat, pharynx and larynx as well as in extrathoracic areas including the larger bronchiole, bronchi and trachea. Despite the higher efficacy of the treatment according to the invention as outlined above, said treatment does not result in any increase of such undesirable side effects. No pharyngeal candidiasis, no pneumonia, no oropharyngeal pain, no dysphonia, hoarseness, and only minor and negligible oral candidiasis in the mouth of only one patient and laryngitis were observed.

Table 6 summarizes results of side effects in the four groups investigated.

TABLE 6

Occurrence of Side Effects Observed by Treatment

|  | ECJN-Bud 1 mg N = 80 | | ECJN-Placebo N = 40 | | ECJN-Bud 0.5 mg N = 39 | | CN-Bud 1 mg N = 40 | |
| --- | --- | --- | --- | --- | --- | --- | --- | --- |
| Dysphonia | 0 | 0.0 | 1 | 2.5 | 1 | 2.6 | 0 | 0.0 |
| Oropharyngeal Pain | 0 | 0.0 | 1 | 2.5 | 0 | 0.0 | 0 | 0.0 |
| Oral Candidiasis | 1 | 1.3 | 0 | 0.0 | 0 | 0.0 | 0 | 0.0 |
| Oropharyngeal Candidiasis | 0 | 0.0 | 1 | 2.5 | 0 | 0.0 | 0 | 0.0 |

ECJN-Bud = Inhalable Budesonide administered by the electronically controlled jet nebulizer;
ECJN-Placebo = Saline administered by the electronically controlled jet nebulizer;
CN-Bud = Budesonide delivered by the PARI conventional nebulizer As seen in Table 6, there was no relevant increase in the side effects typically associated with inhalation of high doses of corticosteroids in the ECJN-Bud/1.0 mg group. When dysphonia, oropharyngeal pain, oral candidiasis and oropharyngeal candidiasis were investigated vis-à-vis each treatment group, only one patient reported presence of oral candidiasis in the ECJN-Bud/1 mg group with no other side effects being observed, whereas in the control group one case of pharyngeal candidiasis, one case of oropharyngeal pain and one case of dysphonia were observed. This further confirms safety, tolerability and effectiveness of the instant method and system for treatment of severe oral corticosteroid-dependent asthma.

Serum Cortisol Levels

As discussed above, severe asthma treated with steroids may lead to suppression of endogenous production of hydrocortisone (cortisol). As a consequence, when the oral administration of corticosteroids is stopped or decreased too rapidly, a life-threatening acute adrenal crisis caused by insufficient levels of cortisol may develop because the adrenal glands of the patient are unable to produce their own hormones fast enough in response to any stress situation.

To determine if the replacement of oral corticosteroids with instant inhalable corticosteroids affects the endogenous production of cortisol, levels of cortisol in plasma of studied subjects were determined. The results for the endogenous serum cortisol levels indicate that severe asthma patients of all four studied groups entered the study with a suppression of their HPA axis and that such HPA axis would at least partially recover after the inhalation therapy of the invention. These results would further indicate that the corticosteroids delivered by inhalation are advantageous for the patient when compared to orally administered corticosteroids as a major portion of the inhaled corticosteroid would be deposited in the small airways of the lungs, with only a small portion of the dose being transported to the blood stream and thus having much smaller suppressive effect on the HPA axis and on the resulting production of endogenous cortisol.

Efficacy of the Budesonide Inhalation

Serum levels of inhalable budesonide delivered according to the invention show dose response to the inhalation as well as, but to a lesser degree, to the used device.

For budesonide serum concentration analysis, blood was drawn in all four investigated groups either before inhalation or 30-60 minutes following inhalation at baseline (post-inhalation) and at week 18 (pre- and post-inhalation). Results are seen in FIG. 10.

FIG. 10 shows a clear dose response for budesonide serum levels as can be seen when comparing the serum levels of full and half dose groups ECJN-Bud/1 mg and 0.5 mg. The three bars in FIG. 10 for each group denote levels at baseline (solid bar); levels at week 18, pre-inhalation (hatched bar); and levels at week 18, post-inhalation (dotted bar).

As seen in FIG. 10, all budesonide treated groups showed a clear increase of the budesonide serum levels after budesonide inhalation, as was expected. Budesonide serum concentrations for the ECJN-Bud/0.5 mg and ECJN-Bud/1 mg groups exhibited dose proportionality with e.g. post-inhalation levels of about 800 µg/ml and about 1650 µg/ml at baseline, respectively. Further, inhalation in the ECJN-Bud/1 mg group resulted in an over two-fold increase of serum budesonide levels compared to the CN-Bud/1 mg group, and serum budesonide levels following treatment with only half the dose of budesonide (ECJN-Bud/0.5 mg) were not significantly different from those following treatment with CN-Bud/1 mg (independent t-test, equal variance, $\alpha$=0.05). This shows the superiority of the instant invention and highlights the inefficacy of the conventional inhalation treatment without flow rate and volume control.

Drug accumulation can occur if the dosing interval is shorter than the elimination half-life. The dosing interval for ECJN-Bud is roughly 12 hours (bi-daily) whereas the published elimination half-life for budesonide is 2.2-4.5 hours after IV or inhalation administration. Evaluation of the temporal trend of budesonide serum levels from baseline to week 18 indicates that budesonide did not accumulate in serum over the 18-week treatment period; i.e., baseline post-inhalation mean serum budesonide concentrations were not significantly different from week 18 post-inhalation levels (independent t-test, equal variance, $\alpha$=0.5).

Drug and Device Combination System for Flow and Volume Regulated Inhalation

A complete or partial reduction in use of oral corticosteroids for treatment of severe, oral corticosteroids-dependent asthma or other respiratory diseases is achieved with a novel drug and device combination system that effectively controls the flow rate and inhalation volume of the inhalable corticosteroid into the patient's lungs and selectively deposits the inhalable drug in the target area, i.e., small airways of the peripheral lungs.

Drug and Device Combination System

Drug and device combination system of the invention comprises of an inhalable corticosteroid and of the electronically controlled inhalation device, such as a jet nebulizer. The drug is an inhalable corticosteroid. The device used in the above described studies with budesonide is a modified, manually triggered PARI LC® Star nebulizer that is enhanced with an electronic control unit. While the nebulizer part generates and delivers the corticosteroid containing aerosol, the electronic control unit assures the compliance with an optimal breathing maneuver programmed individually for each patient and logged and saved on an individual therapeutic protocol card inserted into the device. The electronic control unit further comprises preselected settings for the treatment protocol, such as personal volume and flow rate settings, number of breaths vis-à-vis delivered volume, a monitored compliance with the individual treatment protocol, delivery of the same dose during each treatment, automatic disconnection of the device in case of malfunction or overdosing, automatic conclusion of the therapy once the predetermined dose is inhaled.

The inhalable corticosteroids suitable for treatment of oral corticosteroid-dependent asthma or other respiratory disease needing oral corticosteroid treatment are naturally or synthetically prepared corticosteroids that are suitable for delivery by inhalation. Exemplary inhalable corticosteroids are budesonide, fluticasone, beclomethasone dipropionate, mometasone furoate, ciclesonide, flunisolide and triamcinolone acetonide. Also included in this group are any other inhalable corticosteroids that may be currently available, are currently in development or may become available in the future.

Inhalable Corticosteroids Dosing

While the representative corticosteroid budenoside was tested and found to be efficacious for treatment of severe oral corticosteroid-dependent asthma or another respiratory disease requiring treatment with oral corticosteroids when delivered in the daily dose of 1 or 2 mg/day, such dose may be adjusted to be from 0.2 to 0.8 mg delivered from 1 to 4 times a day, with maximum daily dose for inhalation not to exceed 3.2 mg/day. Preferable dose for treatment of severe asthma is from 0.5 to about 1 mg delivered twice a day (BID).

Inhalable fluticasone dose for treatment of patient with oral corticosteroid-dependent asthma or another respiratory disease requiring treatment with oral corticosteroids is from about 0.1 mg to about 1 mg delivered BID, with preferable dose 0.88 mg BID. The maximum daily dose should not exceed 2.5 mg, preferably should not be higher than 1.6 mg/day.

Inhalable flunisolide dose for treatment of patient with oral corticosteroid-dependent asthma or another respiratory disease requiring treatment with oral corticosteroids is from about 0.5 mg to about 1 mg delivered BID, with preferable dose 1 mg BID. The maximum daily dose not to exceed 3 mg, preferably not over 2 mg/day.

Inhalable triamcinolone acetonide dose for treatment of patient with oral corticosteroid-dependent asthma or another respiratory disease requiring treatment with oral corticosteroids is from about 200 μg to about 800 μg. Preferred inhalable dose delivered BID is from about 150 μg to about 300 μg. The maximum daily dose not to exceed 2000 μg, preferably not over 800 μg.

Inhalable beclomethasone dipropionate dose for treatment of patient with oral corticosteroid-dependent asthma or another respiratory disease requiring treatment with oral corticosteroids is from about 0.1 mg to about 0.8 mg delivered BID, with preferable dose 0.5 mg BID. The maximum daily dose not to exceed 2 mg, preferably not over 1 mg/day.

Inhalable mometasone dose for treatment of patient with oral corticosteroid-dependent asthma or another respiratory disease requiring treatment with oral corticosteroids is from about 0.1 mg to about 0.5 mg delivered BID, with preferable dose 0.25 mg BID. The maximum daily dose not to exceed 2 mg, preferably not over 0.5 mg/day.

Inhalable ciclesonide dose for treatment of patient with oral corticosteroid-dependent asthma or another respiratory disease requiring treatment with oral corticosteroids is from about 0.05 mg to about 0.6 mg delivered BID, preferably from 0.08 mg to 0.4 mg BID. The maximum daily dose not to exceed 2 mg, preferably not over 1 mg/day.

The Device Comprises a Nebulizer Unit and an Electronic Control Unit

The device of the invention comprises of three parts, namely of the nebulizer, the compressor, the airflow control pump and the electronic control unit including a pre-programmable therapeutic protocol card. The device is seen in FIG. 11.

The nebulizer unit 12 of the device 10 is an appropriately set-up basic PARI® LC Star jet nebulizer designed for delivering the aerosolized inhalable corticosteroid into the target areas of the lungs in high dose in short inhalation time. However, any other type of nebulizer unit, such as other jet nebulizers, ultrasonic nebulizers, or vibrating mesh nebulizers can be coupled with the device 10. The PARI® LC Star jet nebulizer unit is a continuous nebulizer equipped with valve system having a high aerosol output of from about 0.20 to about 0.35 ml/min, typically about 0.23-0.25 ml/min. The nebulizer uses a breath-enhanced delivery and is able to predominantly (more than 75%) generate particles having substantially optimal mean particle size of between 1 and 5 μM, preferably about 3.0 to 4.0 μm, and most preferably about 3.8 μm (MMAD) with geometric standard deviation (GSD) of less than 2.5. The nebulizer has a container 20 with approximately 6 ml of total capacity and further comprises the mouthpiece 22 and a tube 24 connecting the nebulizer to the airflow control pump which provides the air flow to assist inspiration and for the control of flow rate and volume, and a tube 26 connecting the nebulizer to the compressor 28 for generating the drug aerosol. Both, the compressor and the airflow control pump are placed in the same case 16 that also holds the electronic control unit 14. The nebulizer is adjusted to minimize waste of the drug in extrathoracic space and to maximize the amount of the drug deposited in the small airways of the lungs and to deliver about 80% of the drug filling dose in the respirable range of particles smaller than 5 μm within a treatment duration of from about 10 to about 14 minutes.

The electronic control unit 14 comprises a means for controlling the breathing pattern of a patient, e.g. by providing a predefined inspiratory flow rate and a predefined inhalation volume. Moreover, it is configured to deliver an aerosol using the bolus technique as defined above.

The electronic control unit further includes a display 30. The display 30 provides a patient friendly therapy support (e.g., by displaying feedback messages when patient inhales too fast), has adjustable settings for patient-specific inhalation volume, flexible volume regulation, instructions for therapy, feedback on inhalation and complete information on unit progress.

Furthermore, the unit has a slit 34 where the therapeutic protocol card 32, containing individualized drug and treatment-specific information, is inserted for each individual patient. This therapeutic protocol card 32 stores logged drug data (e.g., type of drug, filling dose and required daily dose) and information on the individual patient (e.g., his/her most appropriate pre-set inhalation volume) required by the electronic control unit. It further records all therapy-related data for compliance monitoring as described below.

The drug-specific therapeutic protocol card 32 is an electronic chip card that is designed to transfer all relevant therapy parameters, such as the drug and dose-specific inhalation information to the electronic control unit, and that assures delivery of the inhalable corticosteroid in the right dosage to the target site of the lungs. These therapy parameters depend on the patient's conditions and required treatment.

The therapeutic protocol card provides information for a specific corticosteroid drug and its respective recommended dosage and desired deposition area in the lungs. Depending on individual subject's inspiration capacity (IC), a physician, nurse or a patient can select the personal inhalation volume. In a better, less variable alternative, the lung function of a patient is based on FEV1 determinations which then allow the selection of an appropriate inhalation volume to be pre-set for the individual patient, based on empirical data as seen exemplary in Table 7. In cooperation between physician and patient, an initial volume as high as is well tolerable for the patient will be chosen.

TABLE 7

| FEV1 [L] | | |
|---|---|---|
| FEV1 % of predicted 51-79% | FEV1 % of predicted 40-50% | Pre-set Inhalation Volume [ml] |
| 0.47-0.70 | 0.39-0.56 | 400 |
| 0.71-0.95 | 0.57-0.77 | 600 |
| 0.96-1.18 | 0.78-0.95 | 800 |
| 1.19-1.42 | 0.96-1.15 | 1000 |
| 1.43-1.66 | 1.16-1.33 | 1200 |
| higher than 1.67 | higher than 1.34 | 1400 |

Of course, if the patient is able to tolerate an inhalation volume higher than 1400 ml, such higher volume will be selected, e.g., 1600, 1800 or 2000 ml. Typically, the inhalation volume will be from about 400 ml up to about 2000 ml. Based on each patient's specific inhalation volume, the electronic control unit then calculates the number of breaths necessary to inhale the required lung dose. The treatment automatically finishes when the complete lung dose has been inhaled (i.e., the calculated number of breaths being taken) and therefore, both under and over dosing can be prevented. The therapeutic protocol card in combination with the electronic control unit enables the patient at all times—even during one inhalation treatment—to choose a higher or lower volume if better tolerated; the device will then simply re-calculate the number of breaths (still) required for the complete administration of the required dose.

The therapeutic protocol card provides the information for an inhalation treatment on the drug (budesonide), the filling dose (1 mg/2 ml) and on the number of breaths needed to complete treatment when a certain flow rate and inhalation volume is selected. Representative information for setting up the individual inhalation volume, the resulting approximate number of breaths required to administer the complete dose and the approximate duration of one inhalation treatment is seen exemplary in Table 8. (For reasons of simplicity the ratio of inhalation and exhalation period is assumed to be 1:1. It is, however, acknowledged that for severely asthmatic patients said ratio can shift to even 0.4:1, thus potentially increasing the treatment duration.)

TABLE 8

| Breath [sec] (inspiration + exhalation) | Inspiration period [sec] | Nebulization period [sec] (Aerosol Bolus) | Flow rate [ml/sec] | Volume inhaled [ml] | No. of breaths needed to complete treatment | Approx. treatment duration [min] |
|---|---|---|---|---|---|---|
| 4 | 2 | 1 | 200 | 400 | ~273 | 18 |
| 6 | 3 | 2 | 200 | 600 | ~136 | 14 |
| 8 | 4 | 3 | 200 | 800 | ~91 | 12 |
| 10 | 5 | 4 | 200 | 1000 | ~68 | 11 |
| 12 | 6 | 5 | 200 | 1200 | ~55 | 11 |
| 14 | 7 | 6 | 200 | 1400 | ~45 | 11 |
| 16 | 8 | 7 | 200 | 1600 | ~39 | 10 |
| 18 | 9 | 8 | 200 | 1800 | ~34 | 10 |
| 20 | 10 | 9 | 200 | 2000 | ~30 | 10 |

Active Agent: Budesonide
Filling Dose: 1 mg/2 ml (ampoule)

As seen from Table 8, when for example the inhalation volume is selected to be 400 ml, inhalation period 2 seconds, with a nebulization period of 1 second, then 273 breaths are needed to complete treatment and to deliver the complete 2 ml filling dose (equals 1 mg budesonide) to the lungs. If the inhalation volume is selected to be 1000 ml, the inhalation time is 5 seconds which favorably expands the nebulization period to 4 seconds; then only 68 breaths are necessary to completely deliver the whole dose.

All accumulated therapeutic data are saved on the therapeutic protocol card for compliance analysis, which is important for evaluation of efficacy of the treatment because doctors and patients can analyze the treatment protocol and change it as appropriate.

Therapeutic parameters stored for compliance analysis and monitoring include for example the date, onset and duration of each single inhalation treatment, timing of inhalation (morning vs. evening), inhaled dose per day, the chosen inhalation volume setting and changes thereof, the number of breaths taken, data on whether each single inhalation treatment was finished successfully or was interrupted, whether the patient inhaled too fast, whether the pressure at the mouthpiece was too high or too low, whether treatments were missed (usually bi-daily inhalation treatments), but also more technical information on the operation of the device such as error codes for certain events like "compressor damaged" or "wrong tubing attached". Thus, inhalation therapy with the device of the invention can be specifically adapted based on the patient and his individual conditions. The device therefore provides the optimal solution for the therapeutic inhalation of aerosolized corticosteroids.

Flow Rate and Volume Regulated Inhalation

The drug and device combination system of the invention provides flow rate and volume regulated inhalation and thereby delivers the drug selectively to a target area of small airways of the lungs.

Pulmonary deposition studies investigated the extent and pattern of pulmonary deposition of the inhaled budesonide when the inhalation had a regulated flow rate and volume. Results seen in FIG. 12 show that when the flow rate and volume are set to 200 ml/sec and 1800 ml, respectively, there is a substantial increase of the drug deposition in the target area if the generated aerosol has a mean particle size predominantly between 1 and 5 μm. Thus the flow-controlled, slow inhalation at about 200 ml/sec enables maximum drug deposition in the target area of small airways. As further seen in FIG. 12, such inhalation method leads to an alveolar drug deposition of 40 to 50%. In contrast, alveolar deposition is below 10% when using a high inspiratory flow rate of 1000 ml/sec and a small inhalation volume of 350 ml, and it is 20-30% when using an inspiratory flow rate of 1000 ml/sec and an inhalation volume of 1800 ml. It is thus preferred to combine the controlled, slow flow rate of e.g. 200 ml/sec with higher inhalation volumes. As mentioned above, said inhalation volumes depend on the individual patient's lung function and the severity grade of the pulmonary disease, but in cooperation between physician and patient, a volume as high as is well tolerable for the patient can be chosen (see also Table 7). Given that asthma conditions will improve significantly during the improved therapy with a drug and device combination system according to this invention, the majority of patients are enabled to increase their tolerable inhalation volume during the course of said therapy.

Furthermore, as seen in FIG. 13A, the flow rate and volume controlled inhalation also results in decreased secondary side effects because the major corticosteroid portion is deposited in the peripheral area of the lungs. In contrast, unregulated breathing, as seen in FIG. 13B, leads to a substantial portion of the drug being deposited in the extrathoracic area and only a small amount is deposited in the peripheral lungs. As seen in FIG. 13A such controlled slow inhalation results in homogeneously distributed drugs in the target peripheral lungs; i.e., there is not only higher lung deposition but also better dose reproducibility. The controlled, slow inhalation enables maximum drug deposition in the small airways and reduction of deposition of the drug in oropharyngeal area and thereby also reduces undesirable side effects.

The method of the invention thus provides for drug targeting to the small airways of the lungs by flow rate and volume controlled inhalation and further by administering the aerosolized drug as a bolus. According to the bolus technique, the drug-containing aerosol is not delivered throughout the complete duration of the inhalation phase of a breathing maneuver. Rather, it is emitted from the inhalation device only during a specifically selected fraction of the inhalation phase. In other words, the inhalation time (or inspiration time) is subdivided into phases of variable duration. For example, during a first optional phase of the inhalation time, only aerosol-free air is delivered from the inhalation device. In a second phase, following the first phase and sometimes referred to as the nebulization phase or nebulization period, the aerosol (i.e. the aerosolized drug) is delivered; the aerosol delivered in this phase may represent the aerosol bolus. In a third phase, following the second phase, aerosol-free air is again delivered.

It has been found that the bolus technique can be used to transport the drug containing aerosol to a predefined region in the lungs. The shorter the duration of the first period for particle-free air the deeper the target area which will be reached by the subsequently administered aerosol bolus in the second period. Optionally, the duration of the first period can be zero. The third period of particle-free air results in "pushing" the aerosol bolus deeper into the lungs, thereby clearing the upper airways from aerosolized drug particles, and allowing the aerosol particles time to settle, which minimizes their undesired exhalation from the upper lungs and from the oropharyngeal area. Therefore, the duration of the third period which follows the aerosol bolus is typically far longer than the first period, if deeper deposition in the lungs is desired. In one specific embodiment of this invention, the duration of said third period is constant at 1 second while the first period was omitted, as is shown in the example of Table 8.

Inspiration of the bolus is typically achieved through the mouthpiece of the nebulizer. Expiration is typically done without the mouthpiece; this turned out to be more agreeable for most asthma patients.

Although the most favorite and preferable flow rate and volume is as set above, the severe conditions experienced by patients with oral corticosteroid-dependent asthma require that the inhalation volume be flexible depending on the pulmonary status of the patient and thus they often need to be individualized. The instant drug and device combination system including the method and therapeutic protocol permits such individualization as described earlier.

Based on the patient's individual pulmonary status, the individual patient's inhalation therapy is dependent on the inspiration volume said patient can handle and thus the number of breaths the patient must take in order to receive a certain required dose. More severely affected patients with low FEV1 typically take a higher number of breaths with a lower inhalation volume while patients with less severe asthma with higher FEV1 take a lower number of breaths with a higher inhalation volume. It has to be remembered that the drug is administered using an aerosol bolus technique; i.e. the nebulization period (when drug-containing aerosol is administered) is always a bit shorter than the inspiration period, as also shown exemplary in Table 8. This means that the drug-containing "nebulization volume" per breath is also slightly smaller than the preset inhalation volume. Consequently, the administered lung dose of the inhalable corticosteroid is calculated based on number of breaths multiplied by "nebulization volume" per breath.

Additionally, in many cases of severe asthma and lung obstruction, the method can be further enhanced by using inhalation with overpressure. The device and the method therefore further provide means to deliver the corticosteroid aerosol to the patient's lungs under mild overpressure from about 0.1 mbar to no higher than 40 mbar. Such overpressure allows the aerosol to be actively forced to the small alveoli and bronchioles of the airways without causing damage to the lungs and is typically achieved with the compressor and/or airflow control pump unit built into the device. Such unit may be optionally further equipped with a timer so that the overpressure period is limited strictly to the inspiration time. In some device configurations, the air flow (or aerosol flow) provided by the inhalation device is triggered by the onset of a patient's inspiration. Because the air flow (or aerosol flow) is then provided with an overpressure, the patient's breathing effort is reduced. Consequently, patients with severe asthma or with other respiratory diseases characterized by lungs obstructions are able to perform a deeper and slower breathing pattern, compared to spontaneous inhalation without overpressure.

During the inhalation, the airflow control pump and/or the compressor provides a slight overpressure to the aerosol (or particle-free air) to allow preferable deposition of the aerosolized drug into the small airways and prevent its removal during expiration. During expiration, the overpressure is not applied and the patient exhales normally, without any airflow or overpressure being applied.

When the patient inhales from the mouthpiece, the pressure sensor responds and starts the delivery of an air flow by providing a positive overpressure or opening of an inspiration valve. This overpressure, which can be measured at the mouthpiece during inhalation, is different from the pressure or from the pressurized air stream which is used by a jet nebulizer to aerosolize a liquid into an aerosol. The overpressure lasts for the entire inspiration time. When the inspiration time is preselected (via the pre-selected inhalation volume and flow rate), the overpressure is automatically stopped or shut off at the end of the inspiration time because the compressed air supply is interrupted by the device at this time. After a period allocated for exhaling, the process is repeated on and off for the entire period of a single treatment, preferably for less than 11 minutes.

When this method of delivery is selected, during the inspiration time the aerosolized corticosteroid is forced under the overpressure, and—in particular if the bolus technique is used—into the lower lungs. When the overpressure is withdrawn and the patient exhales, the drug forced into the lower lungs is not easily displaced and remains there, resulting in substantially higher deposition of the drug in the peripheral lungs than would happen with a normal breathing without overpressure. During the exhalation time, the small amount of the drug that is exhaled is the one that was in the upper lungs at the last moment of the inspiration time. Some fraction of this small amount may be deposited in the upper lungs or oropharyngeal area but most of it is exhaled.

The device of the invention has a specified flow rate which may be selected between about 100 and 400 ml/sec, preferably 200 ml/sec, i.e. 12 L/min. In this regard, the device controls the flow rate. Once the patient triggers the system by beginning to inhale, the device provides said specified flow rate of preferably 12 L/min (±20%). The slight pressure drop at the mouthpiece caused by the onset of the patient's inspiration triggers the flow rate controlled air flow which in turn guides the patient's inhalation. The breathing pattern is followed by the electronic control unit of the inhalation device and may be displayed on the display as a display message. Any error in inhalation pattern or breach of the therapeutic protocol or non-compliance is noted. For example, an error message would be generated and optionally displayed when the patient would create a negative pressure of less than −10 mbar or when the patient would obstruct the mouthpiece with a pressure of >30 mbar. Due to comfort, most patients end up with a mild overpressure of >0 to 20 mbar. It is to be noted that not all patients inhale with an overpressure but most asthmatic patients use this feature for more comfortable breathing.

Therapeutic Protocol for Inhalable Corticosteroids

Treatment protocol for practicing the instant invention has several parts. First, the suitable corticosteroid is identified and the appropriate dosage for twice a day (BID) delivery is determined. Second, the setting for the inhalation device concerning the air flow rate and volume as well as the filing dose for the corticosteroid is determined. Third, the patient's lung function is evaluated by a physician or even the patient himself. However, it is preferable that at least before or for the initial treatment, the forced expiratory volume per one second (FEV1) of a patient is determined and severity of asthma or other respiratory disease is noted (e.g. by the FEV1% of predicted value) for determination of proper parameters for the therapeutic treatment protocol including the flow rate, inhalation volume, dosage and optionally the overpressure. Fourth, the data are entered on the therapeutic protocol card, and the inhalation device settings are either entered into the display on the electronic unit of the device or read directly from said therapeutic protocol card. Fifth, the corticosteroid filling dose is added to the nebulizer unit of the device. Sixth, the electronically controlled inhalation is initiated.

The appropriate corticosteroid is selected from the group identified above and the appropriate dosage for the selected corticosteroid is determined. Typically, such dosage will be from about 0.1 mg to about 4 mg, delivered by inhalation once to four times a day, preferably about 1 mg dosage per one dosing with twice a day delivery. Most preferred corticosteroids are budesonide and fluticasone.

The appropriate drug dosage is then prepared by dissolution of the required drug dose in an appropriate, preferably aqueous medium or supplied as a ready-to-use filling dose. The filling dose is placed into the container of the nebulizer unit just before the start of the inhalation treatment.

The flow rate is set to be slow between 100 and 400 ml per second, preferably about 200 ml per second. The volume of the air flowing through the inhalation device is preferably set high on between about 400 and about 2000 ml, more preferably between about 1000 ml and about 2000 ml, most preferred about 1400 ml. However, depending on an individual patient's lung function and the severity of his/her disease, a much smaller volume may be selected, such as from 400 ml to 1600 ml, or for example 1000 ml. Preferred particle sizes of the aerosol are based on the target area of the corticosteroid deposition. The target area of the deposition for treatment of severe asthma are the small airways of the peripheral lungs that are best reached with aerosols having mean particle sizes of not smaller than 1 µm and no larger than 5 µm, preferably between 3 and 4 µm, and such as about 3.8 µm (MMAD).

As described earlier, the total number of breaths needed for delivery of the complete dosage of the corticosteroid per one inhalation treatment is based on the severity grade of the patient's condition (established by his/her FEV1 and FEV1% of predicted values). The FEV1 of the patient is determined, typically using a spirometry, to estimate the patient's inspiration capacity (IC) and hence choose an appropriate inhalation volume based on empirical data, as shown exemplary in Table 7. The corresponding number of breaths required to inhale a complete dose using a given filling dose (such as 1 mg/2 ml) is then set by the therapeutic protocol card according to Table 8.

The inhalation volume and the resulting number of breaths required are stored on the therapeutic protocol card so that later on the patient himself can set up the parameters for inhalation, in particular the volume, based on his/her physical conditions and well-being at any time, even during one inhalation treatment.

After all parameters are determined and properly entered into the electronic control unit of the inhalation device (either manually or preferably by the insertion of the therapeutic protocol card having said parameters stored on), the inhalation treatment is initiated. It is a very simple process comprising the following steps. The nebulizer unit is connected to the electronic control unit of the inhalation device, drug is filled into the nebulizer container, the patient is set up with the mouthpiece of the nebulizer and the ON button on the device is pressed to start the inhalation treatment. The inspiratory air flow (or aerosol flow) is automatically switched off once the whole dose is delivered, i.e. the patient will notice that he/she cannot inhale through the mouthpiece anymore after delivery of the total dose. Due to the electronic control of the flow rate and volume as well as constant aerosol particle sizes, every inhalation treatment delivers the same amount of drug to the lower lungs under the same conditions. There is no over or under-dosing. The electronic control unit monitors the progress and compliance of the inhalation with the preset flow rate and inhalation volumes and issues a warning in case the inhalation is too slow or too fast or when some other parameter changes during the inhalation.

The whole device may additionally be provided and supplied as a kit comprising the complete device including the inhalation device and the therapeutic information card, as well as separately supplied corticosteroid(s) in individual ampoules.

The drug and device combination of the invention that is electronically controlled with regard to flow rate and inhalation volume overcomes many problems and errors observed with uncontrolled inhalation treatments.

Commonly observed errors made by the patients during an inhalation maneuver are that their breathing is too fast, their breathing is too shallow or their breathing is not coordinated. When the patient breathes too fast, the high inhalation flow rate results in extremely high drug deposition in the back of the throat and the larynx, with almost no drug deposition in the deep lungs. When the patient's breathing is too shallow, a shallow breath takes on only a small inhalation volume that cannot transport the aerosolized drug particles deep into the lungs thereby resulting in minimal deep lung deposition. When the breathing is not well coordinated, for example when the aerosol production and the inspiration phase of a patient are not in line, there is none or lesser deep lung deposition. Moreover, there are problems with non-compliance. Some patients only take the drug when asthmatic symptoms occur and not continuously in a controllable manner. Patients with a poor breathing maneuver seldom profit from the unregulated inhalation therapy, because they generally do not get a sufficient amount of the drug into the lower lungs. Since these patients also have more side effects caused by the high extrathoracic deposition, an abortion of and withdrawal from inhaled corticosteroid therapy is more likely.

All these problems are advantageously overcome with electronically controlled inhalation using the drug and device combination of the invention.

What is claimed:

1. A drug and device combination system for the treatment of a patient suffering from oral corticosteroid-dependent asthma, said combination comprising:

an inhalable corticosteroid formulation; and an electronically controlled inhalation device adapted to administer the inhalable corticosteroid formulation to the patient as an aerosol predominantly into the small airways of the lower lungs of the patient;

the inhalation device being further adapted to generate the aerosol as a bolus with a mean particle size from about 1 μm to about 5 μm at a controlled flow rate preset to be from 100 ml/second to 400 ml/second;

the inhalation device being further adapted to administer the aerosol with an overpressure of 0.1 mbar to 40 mbar; and the inhalation device being further adapted to administer the aerosol in two or three phases wherein a first phase is optional and consists of administering particle-free air to the patient, wherein said first phase is followed by a second phase consisting of administration of the aerosol comprising the corticosteroid to the patient, and wherein said second phase is followed by a third phase consisting of administration of particle-free air to the patient; and wherein such administration of the inhalable corticosteroid formulation results in:

complete or partial weaning of the patient from the orally administered corticosteroids and an increase of the FEV1-values of the patient.

2. The combination of claim 1, wherein such administration further results in an improvement of Quality of Life of the patient;

decrease of exacerbation symptoms; and decrease of days of hospitalization.

3. The combination system of claim 1, wherein the aerosol is administered with a flow rate of 200 ml/sec.

4. The combination system of claim 1, wherein the aerosol is administered with a controlled volume of from about 400 ml to about 2000 ml.

5. The combination system of claim 4, wherein said volume is from about 1000 ml to about 2000 ml.

6. The combination system of claim 1, wherein the flow rate is preset to be about 200 ml/sec and the volume preset to be from about 1000 ml to about 2000 ml.

7. The combination system of claim 1, wherein said overpressure is from 0.1 mbar to 20 mbar.

8. The combination system of claim 1, wherein said inhalable corticosteroid is provided in the form of a solution or suspension, and wherein a single dose of said corticosteroid is from about 0.1 to about 4 mg.

9. The combination system of claim 8, wherein said inhalable corticosteroid is selected from the group consisting of budesonide, fluticasone, beclomethasone dipropionate, mometasone furoate, ciclesonide, flunisolide and triamcinolone acetonide.

10. The combination system of claim 8, wherein said inhalable corticosteroid is budesonide, and wherein a single dose is from about 0.5 to about 1 mg.

11. The combination system of claim 1, wherein said treatment is accomplished in less than 14 minutes.

12. The combination system of claim 11, wherein said treatment is accomplished in less than 10 minutes.

13. The combination system of claim 1, wherein said treatment is administered once to four times a day.

14. The combination system of claim 1, wherein the increase in the FEV1 values of the patient allows a dose reduction of the orally administered corticosteroids by at least 50% or more in up to about 80% of all patients treated with said combination system.

15. The combination system of claim 14, wherein the dose of the orally administered corticosteroids is reduced to zero in at least 50% of all patients treated with said combination system.

16. The combination system of claim 1, wherein said electronically controlled inhalation device comprises an electronic control unit, and wherein one or more individual therapeutic parameter(s) of the patient are entered manually into said electronic control unit or are read from an electronic data storage device or a therapeutic protocol card.

17. The combination system of claim 16, wherein said therapeutic parameter(s) comprise inspirational flow rate, inhalation volume, selected corticosteroid, selected dose, selected concentration in the corticosteroid formulation, and a number of breaths needed for delivery of the total dosage.

18. The combination system of claim 17, wherein said therapeutic protocol card is further set to store therapy-related data for compliance analysis and wherein such data include date, onset and duration of each inhalation treatment, an inhaled dose, a change of the inhalation volume settings, a number of breaths taken, data providing information on each single inhalation treatment, on treatment conclusion or interruption, on inhalation pattern and speed, on a high or low pressure at the mouthpiece, and on the missing treatments.

19. The combination system of claim 2, wherein said treatment results in complete weaning from any orally administered steroids in at least 50% of all treated patients or wherein said system decreases the use of any orally administered steroids to 50% or less of the initial oral corticosteroid dose in at least about 80% of all treated patients.

20. A drug and device combination system for treatment of a patient suffering from oral corticosteroid-dependent asthma, said combination comprising:
   an inhalable budesonide formulation; and
   an electronically controlled jet nebulizer adapted to administer the inhalable budesonide formulation to the patient twice a day as an aerosol predominantly into the small airways of the lower lungs of the patient;
   the electronically controlled jet nebulizer being further adapted to generate the aerosol as a bolus with a mean particle size from about 1 μm to about 5 μm MMAD at a controlled flow rate preset to be about 200 ml/second;
   the electronically controlled jet nebulizer being further adapted to administer the aerosol in two or three phases wherein a first phase is optional and consists of administering particle-free air to the patient, wherein said first phase is followed by a second phase consisting of administration of the aerosol comprising budesonide to the patient, and wherein said second phase is followed by a third phase consisting of administration of particle-free air to the patient;
   the jet nebulizer being further adapted to administer the aerosol at an overpressure from about 0.1 mbar to about 20 mbar; and
   wherein such administration of the inhalable budesonide formulation results in an increase of the FEV1 values of the patient.

21. A method for the treatment of a patient suffering from oral corticosteroid-dependent asthma comprising:
   administering, with an electronically controlled inhalation device, an inhalable corticosteroid formulation predominantly into the small airways of the lower lungs of the patient,
   wherein the inhalation device administers the inhalable corticosteroid formulation as an aerosol bolus at a controlled flow rate preset to be from 100 ml/second to 400 ml/second,
   wherein the aerosol has a mean particle size from about 1 μm to about 5 μm,
   wherein said aerosol is administered in two or three phases wherein a first phase is optional and consists of administering particle-free air to the patient, wherein the first phase is followed by a second phase consisting of administration of the aerosol comprising the corticosteroid to the patient, and wherein the second phase is followed by a third phase consisting of administration of particle-free air to the patient; and
   wherein the aerosol is administered with an overpressure of 0.1 mbar to 40 mbar; and
   wherein the administration of the inhalable corticosteroid formulation results in complete or partial weaning of the patient from the orally administered corticosteroids, and an increase of the FEV1-values of the patient.

* * * * *

UNITED STATES PATENT AND TRADEMARK OFFICE
CERTIFICATE OF CORRECTION

PATENT NO. : 8,834,848 B2  Page 1 of 1
APPLICATION NO. : 13/605451
DATED : September 16, 2014
INVENTOR(S) : Bernard Muellinger et al.

It is certified that error appears in the above-identified patent and that said Letters Patent is hereby corrected as shown below:

On the title page item (73) Assignee:
Please replace "Activaero GmbH Research &Development" with --Activaero GmbH--.

Signed and Sealed this
Eighth Day of September, 2015

Michelle K. Lee
*Director of the United States Patent and Trademark Office*